US011576852B2

(12) United States Patent
Teboul

(10) Patent No.: US 11,576,852 B2
(45) Date of Patent: *Feb. 14, 2023

(54) TWO COAT PROCESS FOR DYEING KERATIN FIBRES

(71) Applicant: Karen Teboul, St. Mande (FR)

(72) Inventor: Karen Teboul, St. Mande (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/411,671

(22) PCT Filed: Jun. 26, 2013

(86) PCT No.: PCT/EP2013/063388
§ 371 (c)(1),
(2) Date: Dec. 29, 2014

(87) PCT Pub. No.: WO2014/001391
PCT Pub. Date: Jan. 3, 2014

(65) Prior Publication Data
US 2015/0174051 A1    Jun. 25, 2015

Related U.S. Application Data

(60) Provisional application No. 61/695,317, filed on Aug. 31, 2012.

(30) Foreign Application Priority Data

Jun. 29, 2012    (FR) ........................... 1256216

(51) Int. Cl.
| | | |
|---|---|---|
| *A61K 8/895* | (2006.01) | |
| *A61Q 5/06* | (2006.01) | |
| *A61K 8/81* | (2006.01) | |
| *A61K 8/02* | (2006.01) | |
| *A61K 8/26* | (2006.01) | |
| *A61K 8/89* | (2006.01) | |
| *A61K 8/19* | (2006.01) | |
| *A61K 8/25* | (2006.01) | |
| *A61K 8/891* | (2006.01) | |

(52) U.S. Cl.
CPC ............ *A61K 8/895* (2013.01); *A61K 8/0241* (2013.01); *A61K 8/19* (2013.01); *A61K 8/25* (2013.01); *A61K 8/26* (2013.01); *A61K 8/81* (2013.01); *A61K 8/8152* (2013.01); *A61K 8/89* (2013.01); *A61K 8/891* (2013.01); *A61Q 5/06* (2013.01); *A61Q 5/065* (2013.01); *A61K 2800/43* (2013.01); *A61K 2800/48* (2013.01); *A61K 2800/621* (2013.01); *A61K 2800/651* (2013.01); *A61K 2800/87* (2013.01); *A61K 2800/884* (2013.01)

(58) Field of Classification Search
CPC .......... A61K 2800/43; A61K 2800/884; A61K 8/89; A61K 8/891; A61K 8/895; A61K 8/25; A61K 8/81; A61K 8/8152; A61K 2800/651; A61K 2800/621; A61Q 5/06; A61Q 5/065

See application file for complete search history.

(56) References Cited

U.S. PATENT DOCUMENTS

| | | | |
|---|---|---|---|
| 2,463,611 | A | 3/1949 | Green et al. |
| 3,175,993 | A | 3/1965 | Weyenberg |
| 3,433,232 | A | 3/1969 | Garrett |
| 3,599,647 | A | 8/1971 | Fabbri |
| 4,578,266 | A | 3/1986 | Tietjen et al. |
| 4,693,935 | A | 9/1987 | Mazurek |
| 4,728,571 | A | 3/1988 | Clemens et al. |
| 4,772,675 | A | 9/1988 | Klosowski et al. |
| 4,871,827 | A | 10/1989 | Klosowski et al. |
| 4,888,380 | A | 12/1989 | Kamis et al. |
| 4,898,910 | A | 2/1990 | Kamis et al. |
| 4,906,719 | A | 3/1990 | Chu et al. |
| 4,962,174 | A | 10/1990 | Bilgrien et al. |
| 4,972,037 | A | 11/1990 | Garbe et al. |
| 5,059,414 | A | 10/1991 | Dallal et al. |
| 5,162,410 | A | 11/1992 | Sweet |
| 5,246,694 | A | 9/1993 | Birthwistle |

(Continued)

FOREIGN PATENT DOCUMENTS

| | | |
|---|---|---|
| CA | 711756 A | 6/1965 |
| CN | 101980690 A | 2/2011 |

(Continued)

OTHER PUBLICATIONS

Non-Final Office Action for co-pending U.S. Appl. No. 14/411,679, dated Oct. 12, 2016.
Final Office Action for co-pending U.S. Appl. No. 14/367,382 (dated Nov. 25, 2016).
Non-Final Office Action for co-pending U.S. Appl. No. 14/367,376 (dated Dec. 1, 2016).
International Search Report and Written Opinion for PCT/EP2013/063388, dated Jan. 8, 2013, published as (WO 2014/001391 A1 on Jan. 3, 2014).

(Continued)

*Primary Examiner* — Lakshmi S Channavajjala
(74) *Attorney, Agent, or Firm* — The Marbury Law Group, PLLC

(57) ABSTRACT

The present invention relates to a process for dyeing keratin fibres, in particular the hair, which consists in applying to the keratin fibres: at least one coat of at least a first composition (i) comprising at least one hydrophobic film-forming polymer, at least one volatile solvent and at least one pigment, and then, after drying, at least a second coat of at least a second composition (ii) comprising at least one hydrophobic film-forming polymer, at least one volatile solvent and at least one pigment, the pigments of compositions (i) and (ii) being qualitatively and/or quantitatively different.

15 Claims, No Drawings

(56) References Cited

U.S. PATENT DOCUMENTS

| | | | |
|---|---|---|---|
| 5,645,609 | A | 7/1997 | Andrean et al. |
| 5,799,669 | A | 9/1998 | Briggs |
| 5,849,318 | A | 12/1998 | Imai et al. |
| 5,874,069 | A | 2/1999 | Mendolia et al. |
| 5,919,441 | A | 7/1999 | Mendolia et al. |
| 5,948,393 | A | 9/1999 | Tomomasa et al. |
| 5,961,665 | A | 10/1999 | Fishman |
| 5,981,680 | A | 11/1999 | Petroff et al. |
| 5,990,479 | A | 11/1999 | Weiss et al. |
| 6,013,682 | A | 1/2000 | Dalle et al. |
| 6,051,216 | A | 4/2000 | Barr |
| 6,106,577 | A | 8/2000 | Audousset et al. |
| 6,225,198 | B1 | 5/2001 | Alivisatos et al. |
| 6,606,943 | B2 | 8/2003 | De Laforcade |
| 6,609,457 | B1 | 8/2003 | De Laforcade |
| 7,026,424 | B2 | 4/2006 | Schafer et al. |
| 7,351,405 | B2 | 4/2008 | De La Poterie |
| 7,357,921 | B2 | 4/2008 | Giroud |
| 7,537,120 | B1* | 5/2009 | Cardenas |
| 7,875,265 | B2 | 1/2011 | Blin et al. |
| 7,942,937 | B2 | 5/2011 | Brun |
| 8,105,393 | B2* | 1/2012 | Suddaby .................. A61K 8/84 8/405 |
| 8,124,914 | B2* | 2/2012 | Yu ............................ A45D 1/04 132/224 |
| 8,137,413 | B2 | 3/2012 | Wood et al. |
| 8,337,822 | B2 | 12/2012 | Brun |
| 8,574,317 | B2 | 11/2013 | Schmelz et al. |
| 10,744,080 | B2* | 8/2020 | Teboul ................. A61K 8/8147 |
| 2002/0023555 | A1 | 2/2002 | Laforcade |
| 2003/0175229 | A1 | 9/2003 | Giroud |
| 2004/0120906 | A1 | 6/2004 | Toumi et al. |
| 2004/0142831 | A1 | 7/2004 | Jager Lezer |
| 2004/0180021 | A1 | 9/2004 | De La Poterie |
| 2004/0182408 | A1 | 9/2004 | De LaForcade |
| 2004/0210024 | A1 | 10/2004 | Schafer et al. |
| 2004/0254325 | A1 | 12/2004 | Kuepfer et al. |
| 2006/0085924 | A1 | 4/2006 | Brun |
| 2006/0093568 | A1 | 5/2006 | Blin et al. |
| 2006/0099164 | A1 | 5/2006 | De La Poterie et al. |
| 2006/0115444 | A1 | 6/2006 | Blin et al. |
| 2006/0116489 | A1 | 6/2006 | Lennon |
| 2006/0127334 | A1 | 6/2006 | Ferrari et al. |
| 2006/0134032 | A1 | 6/2006 | Ilekti et al. |
| 2006/0134044 | A1 | 6/2006 | Blin et al. |
| 2006/0134051 | A1 | 6/2006 | Blin et al. |
| 2006/0147402 | A1 | 7/2006 | Blin et al. |
| 2006/0147403 | A1 | 7/2006 | Ferrari et al. |
| 2006/0216257 | A1 | 9/2006 | Pays et al. |
| 2007/0044249 | A1 | 3/2007 | Lisowski et al. |
| 2007/0224140 | A1 | 9/2007 | Quadir et al. |
| 2008/0127429 | A1 | 6/2008 | Brun et al. |
| 2008/0171010 | A1 | 7/2008 | Brun |
| 2009/0151086 | A1 | 6/2009 | Brun |
| 2009/0193595 | A1 | 8/2009 | Brun et al. |
| 2009/0214458 | A1 | 8/2009 | Brun et al. |
| 2010/0266517 | A1* | 10/2010 | Dingley ................... A61Q 1/02 424/59 |
| 2011/0005546 | A1 | 1/2011 | Müller-Grünow et al. |
| 2011/0028571 | A1 | 2/2011 | Hayakawa |
| 2011/0097289 | A1 | 4/2011 | Viala et al. |
| 2011/0165104 | A1 | 7/2011 | Molenda et al. |
| 2011/0300092 | A1 | 12/2011 | Kambach et al. |
| 2013/0074864 | A1 | 3/2013 | Nuzzo et al. |
| 2015/0007845 | A1 | 1/2015 | Teboul |
| 2015/0125413 | A1 | 5/2015 | Teboul |
| 2015/0132243 | A1 | 5/2015 | Teboul |
| 2015/0164196 | A1 | 6/2015 | Teboul et al. |
| 2015/0174041 | A1 | 6/2015 | Teboul |
| 2015/0274972 | A1* | 10/2015 | Mateu ...................... C08J 3/18 424/59 |

FOREIGN PATENT DOCUMENTS

| | | |
|---|---|---|
| CN | 102274134 A | 12/2011 |
| EP | 0412704 A2 | 2/1991 |
| EP | 0412707 A1 | 2/1991 |
| EP | 0815836 A2 | 1/1998 |
| EP | 0874017 A2 | 10/1998 |
| EP | 1040873 A1 | 10/2000 |
| EP | 1184426 A2 | 3/2002 |
| EP | 1400234 A1 | 3/2004 |
| EP | 1649898 A2 | 4/2006 |
| EP | 2070516 A1 | 6/2009 |
| EP | 2095810 A1 | 9/2009 |
| FR | 2480096 A1 | 10/1981 |
| FR | 2679771 A1 | 2/1993 |
| FR | 2741530 A1 | 5/1997 |
| FR | 2831430 A1 | 5/2003 |
| FR | 2833489 A1 | 6/2003 |
| FR | 2958189 A1 | 10/2011 |
| GB | 2073672 A | 10/1981 |
| JP | 05-017710 A | 1/1993 |
| JP | 07-258460 A | 10/1995 |
| JP | 09-188830 A | 7/1997 |
| JP | 10-158450 A | 6/1998 |
| JP | 10-158451 A | 6/1998 |
| JP | 10-158541 A | 6/1998 |
| JP | 2004202251 A | 7/2004 |
| JP | 2008106067 A | 5/2008 |
| JP | 2008/247761 A | 10/2008 |
| JP | 2008247879 A | 10/2008 |
| JP | 2010524917 A | 7/2010 |
| JP | 2011026263 A | 2/2011 |
| WO | 92/21316 A1 | 12/1992 |
| WO | 93/23446 A2 | 11/1993 |
| WO | 95/00578 A1 | 1/1995 |
| WO | 01/96450 A2 | 12/2001 |
| WO | 03/014194 A1 | 2/2003 |
| WO | 2004/028487 A2 | 4/2004 |
| WO | 2008/142658 A2 | 11/2008 |
| WO | 2010/071777 A1 | 6/2010 |
| WO | 2013/092380 A1 | 6/2013 |
| WO | 2013/092381 A1 | 6/2013 |
| WO | 2013/092382 A1 | 6/2013 |
| WO | 2013/092788 A1 | 6/2013 |
| WO | 2014/001390 A1 | 1/2014 |

OTHER PUBLICATIONS

English abstract for JP 05-017710A (Jan. 26, 1993).
English abstract for JP 07-258460A (Oct. 9, 1995).
English abstract for JP 09-188830A (Jul. 22, 1997).
English abstract for JP 10-158450A (Jun. 16, 1998).
English abstract for JP 10-158451A (Jun. 16, 1998).
International Search Report and Written Opinion for PCT/EP2013/063387, dated Jan. 8, 2013, published as (WO 2014/001390 A1 on Jan. 3, 2014).
Todd, Charles, et al., "Volatile Silicone Fluids for Cosmetic Formulations," Cosmetics and Toiletries, vol. 91, Jan. 1976, pp. 29-32.
Dabbousi, B.O., et al., "(CdSe)ZnS Core-Shell Quantum Dots: Synthesis and Characterization of a Size Series of Highly Luminescent Nanocrystallites," Journal of Physical Chemistry B, vol. 101, 1997, pp. 9463-9475.
Peng, Xiaogang et al., "Epitaxial Growth of Highly Luminescent CdSe/CdS Core/Shell Nanocrystals with Photostability and Electronic Accessibility," Journal of the American Chemical Society, vol. 119, No. 30, 1997, pp. 7019-7029.
English language abstract for FR 2831430A1 (May 2, 2003).
Encyclopedia of Chemical Technology, Fourth Edition, vol. 18, 1996, pp. 171-200.
Non-Final Office Action for copending U.S. Appl. No. 14/367,370, dated Feb. 2, 2016.
Non-Final Office Action for copending U.S. Appl. No. 14/367,376, dated Sep. 17, 2015.
Final Office Action for copending U.S. Appl. No. 14/367,376, dated May 20, 2016.
Non-Final Office Action for copending U.S. Appl. No. 14/367,382, dated Feb. 24, 2016.

(56) References Cited

OTHER PUBLICATIONS

Non-Final Office Action for copending U.S. Appl. No. 14/367,388, dated Jan. 20, 2016.
Machine translation of Notification of Reasons for Refusal for counterpart Application JP2014-547862, dated Nov. 10, 2016.
Machine translation of Notification of Reasons for Refusal for counterpart Application JP2014-547861, dated Nov. 21, 2016.
Machine translation of Notification of Reasons for Refusal for counterpart Application JP2014-547863, dated Nov. 14, 2016.
Machine translation of First Office Action for counterpart Application CN 201380034562.1, dated Jan. 12, 2016.
Machine translation of Second Office Action for counterpart Application CN 201380034562.1, dated Nov. 30, 2016.
Machine translation of First Office Action for counterpart Application CN 201380034576.3, dated Dec. 31, 2015.
Machine translation of Second Office Action for counterpart Application CN 201380034576.3, dated Nov. 17, 2016.
Machine translation of Third Office Action for counterpart Application CN 201280062545, dated Apr. 10, 2017.
Final Office Action for U.S. Appl. No. 14/367,376, dated Jul. 3, 2017.
Non Final Office Action for U.S. Appl. No. 14/367,382, dated Nov. 16, 2017.
Final Office Action for U.S. Appl. No. 14/367,388, dated Sep. 7, 2017.
Final Office Action for U.S. Appl. No. 14/367,370, dated Jun. 16, 2017.
Office Action for counterpart Application EP 12 799 223.8, dated Jun. 1, 2017.
Non final Office Action for U.S. Appl. No. 14/411,679, dated Nov. 30, 2017.
Final Office Action for copending U.S. Appl. No. 14/367,370, dated Nov. 3, 2016.
Final Office Action for copending U.S. Appl. No. 14/367,370, dated Jan. 12, 2018.
Shin-Etsu, "Shin-Etsu Unique Materials," Shin-Etsu, revised Nov. 2010, 20 pages.
Chinese Office Action for counterpart Application No. 201380034576.3, dated Feb. 5, 2018.
Machine translation of Notification of Reasons for Refusal for counterpart Application No. JP2014-547862, dated Nov. 10, 2016.
Office Action for counterpart Application No. EP 12 799 223.8, dated Jun. 1, 2017.
Final Office Action for copending U.S. Appl. No. 14/367,382, dated Aug. 6, 2018.
Non-Final Office Action for copending U.S. Appl. No. 14/367,388, dated Apr. 9, 2018.
Final Office Action for copending U.S. Appl. No. 14/367,376, dated Dec. 21, 2018.
Moss et al., Silicones as a Color-Lock Aid in Rinse-Off Hair Care Products, obtained online at: https://pdfs.semanticscholar.org/e78b/faa6983618b3b3896ad83c50e16a67513de.pdf (Year 2004).
Final Office Action for copending U.S. Appl. No. 14/411,679, dated Oct. 2, 2018.
Non-Final Office Action for copending U.S. Appl. No. 14/367,388, dated Oct. 4, 2018.
Final Office Action for copending U.S. Appl. No. 14/367,370, dated Nov. 19, 2018.
Fang, K. et al., "New high molecular weight silicone polyether emulsions for use in personal care applications," IPCOM000200009SD, Sep. 27, 2010.
Non-Final Office Action for co-pending U.S. Appl. No. 14/367,376, dated Aug. 15, 2019.
Non-Final Office Action for co-pending U.S. Appl. No. 14/367,370, dated Jan. 8, 2020.
Final Office Action for co-pending U.S. Appl. No. 14/367,376, dated Dec. 18, 2019.
Notice of Allowance for co-pending U.S. Appl. No. 14/367,388, dated Sep. 5, 2019.
Final Office Action for copending U.S. Appl. No. 14/367,370, dated Jul. 8, 2020.
"Interpolymer launches new polymers at in-cosmetics," Cosmetics Business, Apr. 8, 2011 (printed on Jul. 2, 2020 from https://www.cosmeticsbusiness.com/news/article_page/Interpolymer_launches_new_polymers_at_in-cosmetics/60339).
Notice of Allowance for copending U.S. Appl. No. 14/367,376, dated Apr. 21, 2020.
Final Office Action for co-pending U.S. Appl. No. 14/367,388, dated Apr. 2, 2019.
Non-Final Office Action for co-pending U.S. Appl. No. 14/411,679, dated Apr. 5, 2019.
Final Office Action for co-pending U.S. Appl. No. 14/367,370, dated Jul. 11, 2019.
Final Office Action for copending U.S. Appl. No. 14/367,370, dated Nov. 10, 2021.
Non-Final Office Action for copending U.S. Appl. No. 14/367,370, dated Mar. 30, 2021.

\* cited by examiner

TWO COAT PROCESS FOR DYEING KERATIN FIBRES

CROSS REFERENCE TO RELATED APPLICATIONS

This is a national stage application of PCT/EP2013/063388, filed internationally on Jun. 26, 2013, which claims priority to U.S. Provisional Application No. 61/695,317, filed on Aug. 31, 2012, as well as French Application No. 1256216, filed Jun. 29, 2012.

The present invention relates to a process for dyeing keratin fibres, which consists in applying to the said fibres a first and a second composition, each composition comprising a hydrophobic film-forming polymer, a volatile solvent and a pigment.

It is known practice, in the field of the dyeing of keratin fibres, in particular human keratin fibres, to dye keratin fibres by different techniques, in particular starting from dye precursors for permanent dyeing (oxidation dyeing) or from direct dyes or pigments for non-permanent dyeing.

For various reasons, such as the wish to partially or totally modify the shade thus given to the head of hair by oxidation dyeing or direct dyeing, or the wish to remove this coloration, the user may be led to partially or totally destroy the dyes thus formed or introduced into or onto the hair. Stripping of the artificial colour is then performed.

This stripping is generally performed via processes using oxidizing or reducing systems.

It may also be desired to lighten the hair by means of a bleaching step, in order for the applied coloration to be subsequently visible.

These steps may result in appreciable degradation of the keratin fibres, which detrimentally affects their cosmetic properties. The hair then has a tendency to become rough, more difficult to disentangle and more brittle.

The present invention is concerned more particularly with the field of non-permanent dyeing performed using pigments (in other words using colouring substances that are insoluble in the composition in which they are present).

Non-permanent dyeing performed using pigments has the advantage, over the techniques mentioned above, of not requiring the use of a prior or simultaneous step of bleaching or stripping of the keratin fibres in order for the coloration to be visible. Pigmented compositions based on hydrophobic film-forming polymers, which can produce a coloured sheathing around the hair, are known, for example. However, depending on the chosen type of pigment, the colour result may be dependent on the initial colour of the hair, and it is also difficult to have a true visual lightening effect with certain pigments. Moreover, certain shades are very difficult to obtain, even by mixing several pigments.

Hair mascaras based on film-forming acrylic polymers and silicones are also known, but the sheathing obtained is not always entirely satisfactory in terms of resistance to external agents such as washing, perspiration and sebum.

It is also possible to colour the hair (coloured sheathing) using a pressure-sensitive adhesive silicone copolymer, in particular a copolymer based on silicone resin and on fluid silicone. Once deposited on the hair, these copolymers have the advantage of providing colour that is persistent. On the other hand, the hair treated is rather rough to the touch.

It is thus sought to obtain a process for dyeing keratin fibres that can produce a desired final colour, which is the same irrespective of the original colour of the keratin fibres on which the coloration is applied, and which shows good remanence.

The aim of the present invention is to provide novel compositions for dyeing keratin materials, and in particular keratin fibres such as the hair, which can produce visible and varied colorations on dark or light hair without it being necessary to lighten or bleach the fibres beforehand, and which shows good resistance to external agents such as washing, perspiration and sebum.

This process consists in applying to keratin fibres a first composition having a defined colour, which can modify the initial colour of the keratin fibres so as to obtain the desired colour result via the application of the second composition onto this first coat, this being achieved irrespective of the initial colour of the keratin fibres, while at the same time preserving the integrity of the keratin fibres.

This process thus makes it possible to broaden the colour range of hair colorations, while at the same time preserving the hair, and to obtain colours that are difficult if not impossible to obtain hitherto since they are dependent on the initial colour of the hair, and this being achieved without proceeding via a preliminary step of bleaching or stripping of the hair.

More precisely, a subject of the present invention is a process for dyeing keratin fibres, in particular the hair, which consists in applying to the keratin fibres:

at least one coat of at least a first composition (i) comprising at least one hydrophobic film-forming polymer, at least one volatile solvent and at least one pigment, and then, after drying the said coat, at least one coat of at least a second composition (ii) comprising at least one hydrophobic film-forming polymer, at least one volatile solvent and at least one pigment, the pigments of compositions (i) and (ii) being qualitatively and/or quantitatively different.

The term "qualitatively and/or quantitatively different" means that, considering all the pigments present in composition 1 and all of the pigments present in composition 2, these two sets differ from each other either by the nature of at least one pigment or by the concentration of at least one pigment.

Preferably:

the first composition produces on the keratin fibres a coloration such that the colour variation $\Delta E1$, expressed in the CIE L*a*b* system, between the fibres dyed with this first composition and the untreated fibres is greater than or equal to 2, and the second composition produces on the keratin fibres a coloration such that the colour variation $\Delta E2$, expressed in the CIE L*a*b* system, between the fibres dyed with the second and first compositions and the fibres treated with the first composition is greater than or equal to 2.

The term "untreated" keratin fibres means the keratin fibres before application of the first and/or second composition, irrespective of their coloration before treatment and irrespective of whether this coloration is natural or artificially obtained.

The term "at least one" is understood to mean "one or more".

The term "comprising a" is understood to mean "comprising at least one", unless otherwise specified.

The colorimetric parameters in the CIE L* a* b* system are measured using a Konica Minolta CM2600d spectrocolorimeter (illuminant D65, angle 10°, specular component included) in which L* represents the intensity of the colour, a* indicates the green/red colour axis and b* the blue/yellow colour axis.

The ΔE values are calculated from the measured L*a*b* values.

ΔE1, which is the colour variation between the untreated keratin fibres and the keratin fibres dyed with the first composition, is obtained from the formula:

$$\Delta E = \sqrt{(L_1^* - L_0^*)^2 + (a_1^* - a_0^*)^2 + (b_1^* - b_0^*)^2}$$

in which $L_1^*$ represents the intensity and $a_1^*$ and $b_1^*$ represent the values measured on keratin fibres dyed with the first composition and $L_0^*$, $a_0^*$ and $b_0^*$ represent the values measured on untreated hair.

ΔE2, which is the colour variation between the keratin fibres treated with the first composition and the keratin fibres dyed with the second and first compositions, is obtained from the formula:

$$\Delta E = \sqrt{(L_2^* - L_1^*)^2 + (a_2^* - a_1^*)^2 + (b_2^* - b_1^*)^2}$$

in which $L_2^*$ represents the intensity and $a_2^*$ and $b_2^*$ represent the values measured on dyed keratin fibres after application of the first and second compositions and $L_1^*$, $a_1^*$ and $b_1^*$ represent the values measured on keratin fibres dyed with the first composition.

According to a first variant, the first and second compositions are applied onto dark keratin fibres.

The term "dark" keratin fibres means keratin fibres with a tone depth of less than or equal to 5 and preferably less than or equal to 4.

It is recalled that the notion of "tone" is based on the classification of natural shades, one tone separating each shade from the shade immediately following or preceding it. This definition and the classification of natural shades are well known to hairstyling professionals and are published in the book "Sciences des traitements capillaires [Hair treatment sciences]" by Charles Zviak, 1988, published by Masson, pp. 215 and 278. The tone depths range from 1 (black) to 10 (very light blond), one unit corresponding to one tone; the higher the figure, the lighter the shade.

According to a second variant, the first and second compositions are applied onto light keratin fibres.

The term "light" keratin fibres means keratin fibres with a tone depth, as defined above, of greater than 5 and preferably greater than or equal to 6.

According to a preferred embodiment, the second composition is applied after total drying of the first coat of first composition.

The drying may be performed in the open air or using a device such as a hairdryer.

A subject of the present invention is also a kit for dyeing keratin fibres, comprising:
  at least a first composition (i) comprising at least one hydrophobic film-forming polymer, at least one volatile solvent and at least one pigment, and
  at least a second composition (ii) comprising at least one hydrophobic film-forming polymer, at least one volatile solvent and at least one pigment,
  the pigments of compositions (i) and (ii) being qualitatively and/or quantitatively different.

The first and second compositions may be applied by finger, with a pen, a pencil, a sponge, a fine brush, a coarse brush, a feather, a container fitted with a foam tip, a spray, an aerograph as described in document FR 2 958 189, or any other instrument.

First and Second Compositions

The first and second compositions of the process according to the invention each comprise at least one hydrophobic film-forming polymer. The hydrophobic polymers present in the first and second compositions may be identical or different.

For the purposes of the invention, the term "polymer" means a compound corresponding to the repetition of one or more units (these units being derived from compounds known as monomers). This or these unit(s) are repeated at least twice and preferably at least 3 times.

The term "film-forming" polymer means a polymer that is capable, by itself or in the presence of an auxiliary film-forming agent, of forming a macroscopically continuous film on a support, especially on keratin materials, and preferably a cohesive film.

The term "hydrophobic polymer" is understood to mean a polymer having a solubility in water at 25° C. of less than 1% by weight.

The term "film-forming" polymer means a polymer that is capable, by itself or in the presence of an auxiliary film-forming agent, of forming a macroscopically continuous film on a support, especially on keratin materials, and preferably a cohesive film.

In one embodiment, the hydrophobic film-forming organic polymer is at least one polymer chosen from the group comprising:
  film-forming polymers that are soluble in an organic solvent medium, in particular liposoluble polymers; this means that the polymer is soluble or miscible in the organic medium and forms a single homogeneous phase when it is incorporated into the medium;
  film-forming polymers that are dispersible in an organic solvent medium, which means that the polymer forms an insoluble phase in the organic medium, the polymer remaining stable and/or compatible once incorporated into this medium. In particular, such polymers may be in the form of non-aqueous dispersions of polymer particles, preferably dispersions in silicone oils or hydrocarbon-based oils; in one embodiment, the non-aqueous polymer dispersions comprise polymer particles stabilized on their surface with at least one stabilizer; these non-aqueous dispersions are often referred to as NADs;
  film-forming polymers in the form of aqueous dispersions of polymer particles, which means that the polymer forms an insoluble phase in water, the polymer remaining stable and/or compatible once incorporated into the water, the polymer particles possibly being stabilized at their surface with at least one stabilizer. These polymer particles are often referred to as lattices; in this case, the composition must comprise an aqueous phase.

Among the hydrophobic film-forming polymers that may be used in the composition of the present invention, mention may be made of synthetic polymers, of radical type or of polycondensate type, polymers of natural origin, and mixtures thereof. Hydrophobic film-forming polymers that may be mentioned in particular include acrylic polymers, polyurethanes, polyesters, polyamides, polyureas, cellulose-based polymers such as nitrocellulose, silicone polymers, polyamide polymers and copolymers, and polyisoprenes.

The film-forming polymer may be chosen from the film-forming polymers described in patent application WO 04/028 487.

The hydrophobic film-forming polymer may especially be chosen from:
a) homopolymers and copolymers of olefins; cycloolefins; butadiene; isoprene; styrene; vinyl ethers, esters or amides; (meth)acrylic acid esters or amides containing a linear, branched or cyclic $C_1$-$C_{20}$ alkyl group, a $C_6$-$C_{10}$ aryl group or a $C_2$-$C_6$ hydroxyalkyl group.

Such homopolymers and copolymers may be obtained from monomers chosen from the group constituted by isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, ethyl (meth)acrylate, methyl (meth)acrylate, tert-butyl (meth)acrylate, tridecyl (meth)acrylate, stearyl (meth)acrylate, hydroxyethyl (meth)acrylate, 2-hydroxypropyl (meth)acrylate, benzyl acrylate and phenyl acrylate, or mixtures thereof. Amides of the acid monomers that may be mentioned include (meth)acrylamides, and especially N-alkyl (meth)acrylamides, in particular of $C_2$-$C_{12}$ alkyl, such as N-ethylacrylamide, N-t-butylacrylamide and N-octylacrylamide; N-di($C_1$-$C_4$)alkyl(meth)acrylamides and perfluoroalkyl (meth)acrylates. The above polymers may also contain as monomers small amounts of an unsaturated carboxylic or sulfonic acid such as acrylic acid, methacrylic acid or AMPS, on condition that the overall nature of the polymer remains hydrophobic.

As other vinyl monomers that may be used, mention may also be made of:

N-vinylpyrrolidone, vinylcaprolactam, vinyl-N—($C_1$-$C_6$) alkylpyrroles, vinyloxazoles, vinylthiazoles, vinylpyrimidines and vinylimidazoles, olefins such as ethylene, propylene, butenes, isoprene and butadienes.

The vinyl polymer may be crosslinked using one or more difunctional monomers, especially comprising at least two ethylenic unsaturations, such as ethylene glycol di(meth)acrylate or diallyl phthalate.

Mention will be made, for example, of the alkyl acrylate/cycloalkyl acrylate copolymer sold by Phoenix Chem. under the name Giovarez AC-5099 ML, the acrylates/$C_{12-22}$ alkyl methacrylate copolymer sold by Röhm & Haas under the name Soltex OPT and vinylpyrrolidone copolymers, such as copolymers of a $C_2$-$C_{30}$ alkene, such as a $C_3$-$C_{22}$ alkene, and combinations thereof. As examples of VP copolymers that may be used in the invention, mention may also be made of the VP/vinyl laurate copolymer, the VP/vinyl stearate copolymer, the butylated polyvinylpyrrolidone (PVP) copolymer, the VP/hexadecene copolymer sold by ISP under the name Ganex V216, the VP/eicosene copolymer sold by ISP under the name Ganex V220, the VP/triacontene copolymer or the VP/acrylic acid/lauryl methacrylate copolymer. Mention may also be made of the copolymers whose CTFA name (4th edition, 1991) is octylacrylamide/acrylates/butylaminoethyl methacrylate copolymer, such as the products sold under the name Amphomer® or Lovocryl® 47 by the company National Starch, and also the copolymers whose CTFA name is acrylates/octylacrylamide copolymer, such as the products sold under the name Dermacryl® LT or Dermacryl® 79 by the company National Starch.

Particular polymers that may be mentioned include:
i) polymers bearing fluoro groups belonging to one of the classes described in the above text, in particular the Fomblin products described in U.S. Pat. No. 5,948,393, and the copolymers of alkyl (meth)acrylate/perfluoroalkyl (meth)acrylate described in patents EP 0 815 836 and U.S. Pat. No. 5,849,318.
ii) polymers or copolymers resulting from the polymerization or copolymerization of an ethylenic monomer, comprising one or more ethylenic bonds, which are preferably conjugated (or dienes). As polymers or copolymers resulting from the polymerization or copolymerization of an ethylenic monomer, it is possible to use vinyl, acrylic or methacrylic copolymers.

In one embodiment, the film-forming polymer is a block copolymer comprising at least one block consisting of styrene units or styrene derivatives (for example methylstyrene, chlorostyrene or chloromethylstyrene). The copolymer comprising at least one styrene block may be a diblock or triblock copolymer, or even a multiblock copolymer, in star or radial form. The copolymer comprising at least one styrene block may also comprise, for example, an alkylstyrene (AS) block, an ethylene/butylene (EB) block, an ethylene/propylene (EP) block, a butadiene (B) block, an isoprene (I) block, an acrylate (A) block, a methacrylate (MA) block or a combination of these blocks. The copolymer comprising at least one block constituted of styrene units or styrene derivatives may be a diblock or triblock copolymer, and in particular of the polystyrene/polyisoprene or polystyrene/polybutadiene type, such as those sold or manufactured under the name Luvitol HSB by BASF and those of the polystyrene/copoly(ethylene-propylene) type or alternatively of the polystyrene/copoly(ethylene/butylene) type, such as those sold or manufactured under the brand name Kraton by Shell Chemical Co. or Gelled Permethyl 99A by Penreco.

Mention may be made, for example, of Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton D-1101 (SBS), Kraton D-1102 (SBS), Kraton D-1107 (SIS), Gelled Permethyl 99A-750, Gelled Permethyl 99A-753-58 (mixture of star block polymer and of triblock polymer), Gelled Permethyl 99A-753-59 (mixture of star block polymer and of triblock polymer), Versagel MD 970 and Versagel MD 960 from Penreco (mixture of star polymer and of triblock polymer in isododecane). According to a particular embodiment, the hydrophobic film-forming polymer is a hybrid acrylic polymer, which is preferably in the form of particles in aqueous dispersion.

The term "hybrid acrylic polymer" is understood to mean, within the meaning of the present invention, a polymer synthesized from at least one compound (i) chosen from monomers having at least one (meth)acrylic acid group and/or esters of these acid monomers and/or amides of these acid monomers and from at least one compound (ii) other than the compounds (i).

The (meth)acrylic acid esters (also known as (meth)acrylates) are advantageously chosen from alkyl (meth)acrylates, in particular $C_1$-$C_{30}$, preferably $C_1$-$C_{20}$ and better still $C_1$-$C_{10}$ alkyl (meth)acrylates, aryl (meth)acrylates, in particular $C_6$-$C_{10}$ aryl (meth)acrylates, or hydroxyalkyl (meth)acrylates, in particular $C_2$-$C_6$ hydroxyalkyl (meth)acrylates.

Mention may be made, among alkyl (meth)acrylates, of methyl methacrylate, ethyl methacrylate, butyl methacrylate, isobutyl methacrylate, 2-ethylhexyl methacrylate, lauryl methacrylate or cyclohexyl methacrylate.

Mention may be made, among hydroxyalkyl (meth)acrylates, of hydroxyethyl acrylate, 2-hydroxypropyl acrylate, hydroxyethyl methacrylate or 2-hydroxypropyl methacrylate. Mention may be made, among aryl (meth)acrylates, of benzyl acrylate and phenyl acrylate.

The (meth)acrylic acid esters which are particularly preferred are the alkyl (meth)acrylates.

According to the present invention, the alkyl group of the esters can be either fluorinated or perfluorinated, that is to say that some or all of the hydrogen atoms of the alkyl group are replaced with fluorine atoms.

Examples of amides of the acid monomers that may be mentioned are (meth)acrylamides, and especially N-alkyl (meth)acrylamides, in particular of a $C_2$-$C_{12}$ alkyl. Mention may be made, among N-alkyl(meth)acrylamides, of N-ethylacrylamide, N-(t-butyl)acrylamide, N-(t-octyl)acrylamide and N-undecylacrylamide.

As compounds (ii) different from the compounds (i), mention will be made, for example, of styrene monomers.

In particular, the acrylic polymer may be a styrene/acrylate copolymer, and especially a polymer chosen from copolymers derived from the polymerization of at least one styrene monomer and at least one $C_1$-$C_{20}$ and preferably $C_1$-$C_{10}$ alkyl acrylate monomer.

As styrene monomers that may be used in the invention, mention may be made of styrene and α-methylstyrene, and preferably styrene.

The $C_1$-$C_{10}$ alkyl acrylate monomer can be chosen from methyl acrylate, ethyl acrylate, propyl acrylate, butyl acrylate, hexyl acrylate, octyl acrylate or 2-ethylhexyl acrylate. Mention may be made, as acrylic polymer synthesized with styrene compound, of the styrene/acrylate(s) copolymers sold under the name Joncryl 77 by BASF, under the name Yodosol GH41F by Akzo Nobel and under the name Syntran 5760 CG by Interpolymer.

Mention may also be made, as compound (ii), of the compounds which interact by a process other than the radical polymerization of unsaturated compounds or the compounds resulting from such a process. Such a process can, for example, be a polycondensation. Mention may be made, as polycondensation, of the formation of polyurethanes, polyesters or polyamides. In addition to the acrylic monomer or monomers, the hybrid hydrophobic film-forming polymer of the invention will then comprise the compound resulting from the condensation process or the compounds which interact in the polycondensation process.

As film-forming hybrid acrylic copolymers of this type, mention may be made especially of the product sold under the reference Hybridur 875 Polymer Dispersion by the company Air Products & Chemicals.

As hybrid film-forming hydrophobic acrylic copolymer, use may also be made of the product sold under the reference Primal HG 1000 by the company Dow.

According to a particular embodiment, the hybrid film-forming acrylic polymer is a copolymer of (meth)acrylic acid ester(s) and of styrene.

Styrene-methacrylate copolymers may also be used, such as the polymers sold under the references OS 129880, OS 129881 and OS 84383 from Lubrizol (styrene-methacrylate copolymer).

In one embodiment, the film-forming polymer is chosen from copolymers of vinyl ester (the vinyl group being directly connected to the oxygen atom of the ester group and the vinyl ester having a saturated, linear or branched hydrocarbon-based radical of 1 to 19 carbon atoms bonded to the carbonyl of the ester group) and of at least one other monomer which is chosen from vinyl esters (other than the vinyl ester already present), α-olefins (containing from 8 to 28 carbon atoms), alkyl vinyl ethers (in which the alkyl group contains from 2 to 18 carbon atoms) or allylic or methallylic esters (containing a linear or branched saturated hydrocarbon-based radical of 1 to 19 carbon atoms, bonded to the carbonyl of the ester group).

These copolymers may be partially crosslinked using crosslinking agents, which may be either of the vinyl type or of the allylic or methallylic type, such as tetraallyloxyethane, divinylbenzene, divinyl octanedioate, divinyl dodecanedioate, and divinyl octadecanedioate.

Examples of these copolymers that may be mentioned include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-di methylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene crosslinked with 0.2% divinylbenzene, and allyl propionate/allyl stearate, crosslinked with 0.2% divinylbenzene.

iii) polyalkenes and copolymers of $C_2$-$C_{20}$ alkenes, in particular polybutene.

iv) polycondensates.

Among the polycondensates that may be mentioned are nonionic polyurethanes, polyurethane-acrylics, polyurethane-polyvinylpyrrolidones, polyester-polyurethanes, polyether-polyurethanes, polyureas and polyurea-polyurethanes, and mixtures thereof. The polyurethanes may be, for example, a copolymer of aliphatic, cycloaliphatic or aromatic polyurethane or of polyurea-polyurethane.

The polyurethanes as defined in the invention may also be obtained from branched or unbranched polyesters or from alkyds comprising mobile hydrogens that are modified by means of a polyaddition with a diisocyanate and an organic difunctional (for example dihydro, diamino or hydroxyamino) co-reagent.

Mention may also be made of polyesters, polyesteramides, fatty-chain polyesters, polyamides and epoxyester resins.

The polyesters may be obtained, in a known manner, by polycondensation of aliphatic or aromatic diacids with aliphatic or aromatic diols or with polyols. Succinic acid, glutaric acid, adipic acid, pimelic acid, suberic acid or sebacic acid may be used as aliphatic diacids. Terephthalic acid or isophthalic acid, or alternatively a derivative such as phthalic anhydride, may be used as aromatic diacids. Ethylene glycol, propylene glycol, diethylene glycol, neopentyl glycol, cyclohexanedimethanol and 4,4-N-(1-methylpropylidene)bisphenol may be used as aliphatic diols.

The polyesteramides may be obtained in a manner similar to that for the polyesters, by means of the polycondensation of diacids with amino alcohols. The polyamides may be obtained in a manner similar to that for the polyesters, by means of the polycondensation of diacids with diamines.

Particular polyesters that may be mentioned include aliphatic polyesters containing $C_{4-50}$ alkyl side chains or polyesters resulting from the condensation of fatty acid dimers, or alternatively polyesters comprising a silicone segment in the form of a terminal block, graft or group, as defined in patent application FR 0 113 920.

b) Silicone Compounds.

The hydrophobic film-forming polymer may also be a polymer comprising at least one silicone portion.

In the text hereinbelow, in accordance with what is generally accepted, the terms "silicone" and "polysiloxane" mean any organosilicon polymer or oligomer of linear or cyclic, branched or crosslinked structure, of variable molecular weight, obtained by polymerization and/or polycondensation of suitably functionalized silanes, and constituted essentially of a repetition of main units in which the silicon atoms are linked together via oxygen atoms (siloxane bond ≡Si—O—Si≡), optionally substituted hydrocarbon-based radicals being bonded directly via a carbon atom to the said silicon atoms. The most common hydrocarbon-based radicals are alkyl radicals, especially $C_1$-$C_{10}$ alkyl radicals, and in particular methyl, fluoroalkyl radicals, aryl radicals and in particular phenyl, and alkenyl radicals and in particular vinyl; other types of radicals which can be bonded, either directly or via a hydrocarbon-based radical, to the siloxane chain are, especially, hydrogen, halogens and in particular chlorine, bromine or fluorine, thiols, alkoxy radicals, polyoxyalkylene (or polyether) radicals and in particular polyoxyethylene and/or polyoxypropylene radicals, hydroxyl or hydroxyalkyl radicals, substituted or unsubstituted amine groups, amide groups, acyloxy or acyloxyalkyl radicals, hydroxyalkylamino or aminoalkyl radicals, quaternary ammonium groups, amphoteric or betaine groups, anionic groups such as carboxylates, thioglycolates, sulfosuccinates, thiosulfates, phosphates and sulfates, needless to say this list not being limiting in any way.

As hydrophobic film-forming polymers comprising at least one silicone portion, mention may be made especially of:

i) silicone resins, which are generally soluble or swellable in silicone oils.

These resins are crosslinked polyorganosiloxane polymers.

The nomenclature of silicone resins is known under the name MDTQ, the resin being described as a function of the various siloxane monomer units it comprises, each of the letters MDTQ characterizing a type of unit.

The letter M represents the monofunctional unit of formula $(CH_3)_3SiO_{1/2}$, the silicon atom being bonded to only one oxygen atom in the polymer comprising this unit.

The letter D means a difunctional unit $(CH_3)_2SiO_{2/2}$ in which the silicon atom is bonded to two oxygen atoms.

The letter T represents a trifunctional unit of formula $(CH_3)SiO_{3/2}$.

The letter Q means a tetrafunctional unit $SiO_{4/2}$ in which the silicon atom is bonded to four hydrogen atoms, which are themselves bonded to the rest of the polymer.

In the units M, D and T defined previously, at least one of the methyl groups may be substituted with a group R other than a methyl group, such as a hydrocarbon-based radical (especially alkyl) containing from 2 to 10 carbon atoms or a phenyl group, or alternatively a hydroxyl group.

Various resins with different properties may be obtained from these different units, the properties of these polymers varying as a function of the type of monomers (or units), of the type and number of substituted radicals, of the length of the polymer chain, of the degree of branching and of the size of the side chains.

Examples of these silicone resins that may be mentioned include:

siloxysilicates, which may be trimethyl siloxysilicates of formula $[(CH_3)_3XSiXO]_xX(SiO_{4/2})_y$ (MQ units) in which x and y are integers ranging from 50 to 80, polysilsesquioxanes of formula $(CH_3SiO_{3/2})_x$ (T units) in which x is greater than 100 and at least one of the methyl radicals of which may be substituted with a group R as defined above, polymethylsilsesquioxanes, which are polysilsesquioxanes in which none of the methyl radicals are substituted with another group. Such polymethylsilsesquioxanes are described in document U.S. Pat. No. 5,246,694.

As examples of commercially available polymethylsilsesquioxane resins, mention may be made of those sold:

by the company Wacker under the reference Resin MK, such as Belsil PMS MK: polymer comprising $CH_3SiO_{3/2}$ repeating units (T units), which may also comprise up to 1% by weight of $(CH_3)_2SiO_{2/2}$ units (D units) and having an average molecular weight of about 10 000, or by the company Shin-Etsu under the references KR-220L, which are composed of T units of formula $CH_3SiO_{3/2}$ and contain Si—OH (silanol) end groups, under the reference KR-242A, which comprise 98% of T units and 2% of dimethyl D units and contain Si—OH end groups, or also under the reference KR-251, comprising 88% of T units and 12% of dimethyl D units and contain Si—OH end groups.

Siloxysilicate resins that may be mentioned include trimethylsiloxysilicate (TMS) resins optionally in the form of powders. Such resins are sold under the reference SR1000 by the company General Electric or under the reference TMS 803 by the company Wacker. Mention may also be made of the trimethyl siloxysilicate resins sold in a solvent such as cyclomethicone, sold under the name KF-7312J by the company Shin-Etsu or DC 749 or DC 593 by the company Dow Corning.

ii) Silicone polyamides of the polyorganosiloxane type, such as those described in documents U.S. Pat. Nos. 5,874,069, 5,919,441, 6,051,216 and 5,981,680.

iii) linear block silicone copolymers

The term "linear block copolymer" means a non-crosslinked copolymer, obtained by chain extension rather than by crosslinking.

The term "block copolymer" (or "sequential copolymer") denotes a polymer comprising at least two different blocks (sequences). Each block of the polymer results from one type of monomer or from several types of different monomers. This means that each block may be composed of a homopolymer or of a copolymer, it being possible for this copolymer constituting the block to be in its turn a random or alternating copolymer.

It should also be noted that the copolymer is "linear"; in other words, the structure of the polymer is neither branched nor star-shaped nor grafted.

The linear block silicone copolymer is advantageously provided in the form of particles in dispersion in an aqueous medium.

The aqueous dispersion of block copolymer particles is a silicone-in-water (Sil/W) emulsion, the oily globules of which are composed of a silicone of high viscosity, so that these globules appear to form as "soft particles".

The size of the linear block silicone copolymer particles can vary widely. Preferably, in the present patent application, the linear block silicone copolymer particles generally have a number-average size of less than or equal to 2 microns and preferably less than or equal to 1 micron.

The aqueous dispersions of linear block silicone copolymer particles used in the composition according to the invention can be chosen in particular from those described in document EP-A-874 017, the teaching of which is incorporated here by reference. According to this document, it is possible in particular to obtain the silicone copolymers constituting these particles by a chain extension reaction, in the presence of a catalyst, starting from at least:
(a) one polysiloxane (i) having at least one reactive group and preferably one or two reactive groups per molecule; and
(b) one organosilicone compound (ii) which reacts with the polysiloxane (i) by a chain extension reaction.

In particular, the polysiloxane (i) is chosen from the compounds of formula (I):

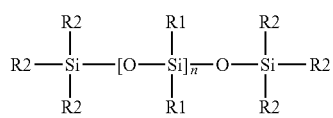

in which $R_1$ and $R_2$ represent, independently of each other, a hydrocarbon-based group containing from 1 to 20 carbon atoms and preferably from 1 to 10 carbon atoms, such as methyl, ethyl, propyl or butyl, or an aryl group, such as phenyl, or a reactive group, and n is an integer greater than 1, provided that there are on average between one and two reactive groups per polymer.

The term "reactive group" means any group that is capable of reacting with the organosilicone compound (ii) to form a block copolymer. Mention may be made, as reactive groups, of hydrogen; aliphatically unsaturated groups, in particular vinyl, allyl or hexenyl groups; the hydroxyl group; alkoxy groups, such as methoxy, ethoxy or propoxy groups; alkoxyalkoxy groups; the acetoxy group; amino groups, and mixtures thereof. Preferably, more than 90% and better still more than 98% of reactive groups are at the chain end, i.e. the radicals $R_2$ generally constitute more than 90% and even 98% of the reactive groups.

n can in particular be an integer ranging from 5 to 30, preferably from 10 to 30 and better still from 15 to 25.

The polysiloxanes of formula (I) are linear polymers, that is to say comprising little branching and generally less than 2 mol % of siloxane units. Furthermore, the groups $R_1$ and $R_2$ may optionally be substituted with amino groups, epoxy groups or sulfur-bearing, silicon-bearing or oxygen-bearing groups.

Preferably, at least 80% of the groups $R_1$ are alkyl groups and better still methyl groups.

Preferably, the reactive group $R_2$ at the chain end is an aliphatically unsaturated group and in particular a vinyl group.

Mention may in particular be made, as polysiloxanes (i), of dimethylvinylsiloxy-polydimethylsiloxane, a compound of formula (I) in which the radicals $R_1$ are methyl radicals and the radicals $R_2$ at the chain end are vinyl radicals while the other two radicals $R_2$ are methyl radicals.

The organosilicone compound (ii) can be chosen from polysiloxanes of formula (I) or compounds acting as chain-extending agent. If it is a compound of formula (I), the polysiloxane (i) will comprise a first reactive group and the organosilicone compound (ii) will comprise a second reactive group which will react with the first. If it is a chain-extending agent, it can be a silane, a siloxane (disiloxane or trisiloxane) or a silazane. Preferably, the organosilicone compound (ii) is a liquid organohydrogenopolysiloxane of formula (II):

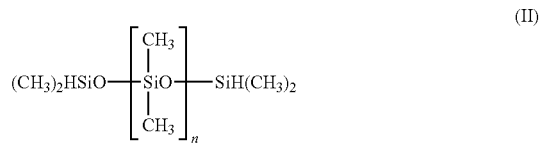

where n is an integer greater than 1 and preferably greater than 10, for example ranging from 2 to 100, preferably from 10 to 30 and better still from 15 to 25. According to a specific embodiment of the invention, n is equal to 20.

The silicone block copolymers used according to the invention are advantageously devoid of oxyalkylene group(s), in particular devoid of oxyethylene and/or oxypropylene group(s).

The catalyst of the reaction between the polysiloxane and the organosilicone compound can be chosen from metals and in particular from platinum, rhodium, tin, titanium, copper and lead. It is preferably platinum or rhodium.

The dispersion of silicone copolymer particles used in the composition according to the invention can in particular be obtained, for example, by mixing (a) water, (b) at least one emulsifier, (c) the polysiloxane (i), (d) the organosilicone compound (ii) and (e) a catalyst. Preferably, one of the constituents (c), (d) or (e) is added last to the mixture, in order for the chain extension reaction to begin only in the dispersion.

As emulsifiers that may be used in the preparation process described above in order to obtain the aqueous dispersion of particles, mention may be made of nonionic or ionic (anionic, cationic or amphoteric) emulsifiers. They are preferably nonionic emulsifiers that may be chosen from polyalkylene glycol ethers of fatty alcohols comprising from 8 to 30 carbon atoms and preferably from 10 to 22 carbon atoms; polyoxyalkylenated and in particular polyoxyethylenated sorbitan alkyl esters, where the alkyl radical comprises from 8 to 30 carbon atoms and preferably from 10 to 22 carbon atoms; polyoxyalkylenated and in particular polyoxyethylenated alkyl esters, where the alkyl radical comprises from 8 to 30 carbon atoms and preferably from 10 to 22 carbon atoms; polyethylene glycols; polypropylene glycols; diethylene glycols; and mixtures thereof. The amount of emulsifier(s) is generally from 1% to 30% by weight, relative to the total weight of the reaction mixture.

The emulsifier used to obtain the aqueous dispersion of particles is preferably chosen from polyethylene glycol ethers of fatty alcohols and mixtures thereof and in particular polyethylene glycol ethers of alcohols comprising 12 or 13 carbon atoms and from 2 to 100 oxyethylene units and preferably from 3 to 50 oxyethylene units, and mixtures thereof. Mention may be made, for example, of $C_{12}$-$C_{13}$ Pareth-3 and $C_{12}$-$C_{13}$ Pareth-23, and mixtures thereof.

According to a particular embodiment of the invention, the dispersion of silicone copolymer particles is obtained from dimethylvinylsiloxypolydimethylsiloxane (or divinyl dimethicone), as compound (i), and from the compound of formula (II) with, preferably, n=20, as compound (ii), preferably in the presence of a catalyst of platinum type, and the particle dispersion is preferably obtained in the presence of $C_{12}$-$C_{13}$ Pareth-3 and $C_{12}$-$C_{13}$ Pareth-23, as emulsifiers.

Use may especially be made, as a dispersion of silicone copolymer particles, of the product sold under the name HMW 2220 by Dow Corning (CTFA name: divinyl dimethicone/dimethicone copolymer/$C_{12}$-$C_{13}$ Pareth-3/$C_{12}$-$C_{13}$ Pareth-23), which is an aqueous 60% dispersion of divinyl dimethicone/dimethicone copolymer comprising $C_{12}$-$C_{13}$ Pareth-3 and $C_{12}$-$C_{13}$ Pareth-23, the said dispersion comprising approximately 60% by weight of copolymer, 2.8% by weight of $C_{12}$-$C_{13}$ Pareth-23, 2% by weight of $C_{12}$-$C_{13}$ Pareth-3 and 0.31% by weight of preserving agents, the remainder to 100% being water.

iv) Grafted silicone compounds

The composition of the invention may also contain a grafted silicone polymer. In the context of the invention, the term "grafted silicone polymer" means a polymer comprising a polysiloxane portion and a portion constituted of a non-silicone organic chain, one of the two portions constituting the main chain of the polymer, the other being grafted onto the said main chain.

The grafted silicone polymers used in the cosmetic composition according to the invention are preferentially chosen from the group constituted by polymers with a non-silicone organic backbone grafted with monomers containing a polysiloxane, and polymers with a polysiloxane backbone grafted with non-silicone organic monomers, and mixtures thereof.

The non-silicone organic monomers constituting the main chain of the grafted silicone polymer may be chosen from radical-polymerizable ethylenically unsaturated monomers, polycondensation-polymerizable monomers such as those forming polyamides, polyesters or polyurethanes, and ring-opening monomers such as those of the oxazoline or caprolactone type.

The polymers with a non-silicone organic backbone grafted with monomers containing a polysiloxane, in accordance with the invention, may be chosen from those described in patents U.S. Pat. Nos. 4,693,935, 4,728,571 and 4,972,037 and patent applications EP-A-0 412 704, EP-A-0 412 707, EP-A-0 640 105 and WO 95/00578. These are copolymers obtained by radical polymerization from ethylenically unsaturated monomers and from silicone macromers containing a vinyl end group, or alternatively copolymers obtained by reaction of a polyolefin comprising functionalized groups and of a polysiloxane macromer containing an end function that is reactive with the said functionalized groups.

The copolymer containing a non-silicone organic backbone grafted with monomers containing a polysiloxane may, for example, have the following structure:

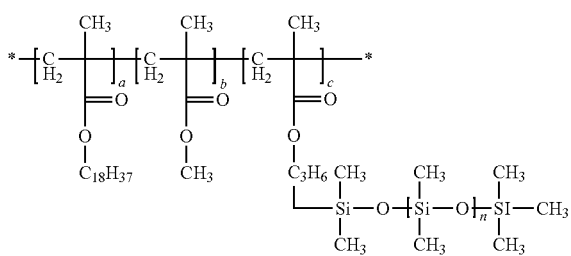

Such a polymer is sold under the name KP 561 by Shin-Etsu.

The copolymer containing a non-silicone organic backbone grafted with monomers containing a polysiloxane may also have the following structure:

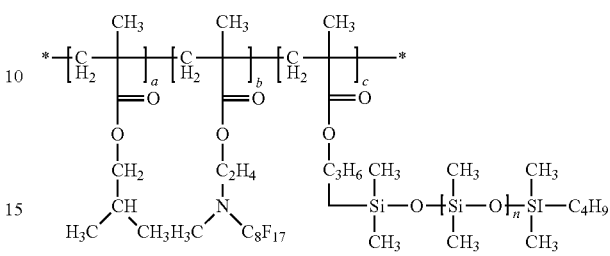

Such a polymer, Polysilicone 7, is sold under the name SA70 by 3M.

Other copolymers containing a non-silicone organic backbone grafted with monomers containing a polysiloxane may also be KP545, KP574 and KP575 sold by Shin-Etsu.

A grafted silicone compound that may also be mentioned is the isobutyl methacrylate/bishydroxypropyl dimethicone acrylate copolymer sold by Grant Industries under the name Granacrysil BMAS.

According to the present invention, the grafted silicone polymer(s), containing a polysiloxane backbone grafted with non-silicone organic monomers, comprise(s) a main silicone chain (or polysiloxane ($\equiv$Si—O—)$_n$) onto which is grafted, within the said chain and also optionally on at least one of its ends, at least one organic group not comprising silicone.

Examples of silicone polymers corresponding to the definition are especially polydimethylsiloxanes (PDMS) onto which are grafted, via a connecting chain unit of thiopropylene type, mixed polymer units of the poly(meth)acrylic acid type and of the polyalkyl (meth)acrylate type. A compound corresponding to this definition that may be mentioned is the polydimethyl/methylsiloxane containing methyl 3-thiopropyl acrylate/methyl methacrylate/methacrylic acid groups or Polysilicone-8 sold under the name VS80 by the company 3M.

Other examples of silicone polymers are especially polydimethylsiloxanes (PDMS) onto which are grafted, via a connecting chain unit of thiopropylene type, polymer units of the polyisobutyl (meth)acrylate type.

Preferably, the number-average molecular mass of the silicone polymers containing a polysiloxane backbone grafted with non-silicone organic monomers of the invention ranges from 10 000 to 1 000 000 approximately and even more preferentially from 10 000 to 100 000 approximately.

Preferably, the grafted silicone polymers are chosen from the group constituted by the copolymer of polydimethylsiloxane-grafted alkyl methacrylate, copolymers of isobutyl methacrylate, of acrylic acid and of silicone macromer, and the poly dimethyl/methyl siloxane containing methyl 3-thiopropyl acrylate/methyl methacrylate/methacrylic acid groups.

v) Polyurea/urethane silicones

The copolymer of the invention may comprise, in addition to the polysiloxane/polyurea, other blocks of different units. Mention will be made in particular of polysiloxane/polyurea/polyurethane block terpolymers.

According to one variant, the copolymer contains solely one or more siloxane blocks and one or more polyurea blocks.

According to the invention, the copolymer may correspond to the general formula (I):

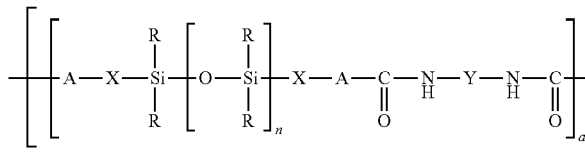

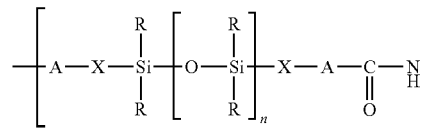

in which:
- R represents a monovalent hydrocarbon-based radical, where appropriate substituted with fluorine or chlorine, containing 1 to 20 carbon atoms,
- X represents an alkylene radical containing 1 to 20 carbon atoms, in which non-neighbouring methylene units may be replaced with —O— radicals,
- A represents an oxygen atom or an amino radical —NR'—,
- Z represents an oxygen atom or an amino radical —NR'—,
- R' represents hydrogen or an alkyl radical containing 1 to 10 carbon atoms,
- Y represents a divalent hydrocarbon-based radical, where appropriate substituted with fluorine or chlorine, containing 1 to 20 carbon atoms,
- D represents an alkylene radical, where appropriate substituted with fluorine, chlorine, $C_1$-$C_6$ alkyl or $C_1$-$C_6$ alkyl ester, containing from 1 to 700 carbon atoms, in which non-neighbouring methylene units may be replaced with —O—, —COO—, —OCO— or —OCOO— radicals,
- n is a number ranging from 1 to 4000,
- a is a number at least equal to 1,
- b is a number ranging from 0 to 40,
- c is a number ranging from 0 to 30, and
- d is a number greater than 0, on condition that A represents in at least one of the units (a) an NH radical.

Preferably, R represents a monovalent hydrocarbon-based radical of 1 to 6 carbon atoms, for example methyl, ethyl, vinyl and phenyl. According to one particular embodiment, R is an unsubstituted alkyl radical.

Preferably, X represents an alkylene radical containing 2 to 10 carbon atoms.

Preferably, the alkylene radical X is not interrupted.

According to one particular embodiment, the group A in all the units (b) and (c), when they are present, represents NH.

According to one particularly preferred embodiment, all the groups A represent an NH radical.

Preferably, Z represents an oxygen atom or an NH radical.

Preferably, Y represents a hydrocarbon-based radical comprising from 3 to 13 carbon atoms, which is preferably unsubstituted. Preferably, Y represents a linear or cyclic aralkylene or alkylene radical.

Preferably, D represents an alkylene radical containing at least 2 and in particular at least 4 carbon atoms, and not more than 12 carbon atoms.

Also preferably, D represents a polyoxyalkylene radical, in particular a polyoxyethylene or polyoxypropylene radical containing at least 20 and in particular at least 100 carbon atoms, and not more than 800 and in particular not more than 200 carbon atoms.

Preferably, the radical D is unsubstituted.

Preferably, n represents a number equal to at least 3 and in particular at least 25, and preferably not more than 800, in particular not more than 400 and particularly preferably not more than 250.

Preferably, a represents a number greater than 50.

When b is other than 0, b preferably represents a number not greater than 50 and in particular not greater than 25.

Preferably, c represents a number not greater than 10 and in particular not greater than 5.

The copolymers of the invention may be obtained according to the polymerization processes described in patent application US 2004/0 254 325 or patent application WO 03/014 194.

According to another embodiment, the copolymer is a nonionic polysiloxane/polyurea copolymer, i.e. it does not contain any ionized or ionizable groups.

Examples of copolymers that may be mentioned include the dimethylpolysiloxane/urea copolymer, of INCI name polyurea dimethicone.

Such a polymer may be obtained especially by copolymerization of an α,ω-aminosilicone with a diisocyanate. Polymers corresponding to these characteristics are, for example, the products sold under the references Wacker-Belsil® UD 60, Wacker-Belsil® UD 80, Wacker-Belsil® UD 140 and Wacker-Belsil® UD 200 by the company Wacker.

vi) Copolymers based on silicone resin and on fluid silicone

These silicone copolymers are obtained by reacting a silicone resin and a fluid silicone. Such copolymers are described, for example, in *Silicone Pressure Sensitive Adhesive*, Sobieski and Tangney, Handbook of Pressure Sensitive Adhesive Technology (D. Satas Ed.), Van Nostrand Reinhold, N.Y.

In the copolymer, the silicone resin is present in a content of between 45% and 75% (relative to the total mass of silicone) and the fluid silicone is present in a content of between 25% and 55%, with the sum of the percentages of silicone resin and of fluid silicone being equal to 100. Preferably, the silicone resin is present in a content of between 55% and 65% (relative to the total mass of silicone) and the fluid silicone is present in a content of between 35% and 45%, with the sum of the percentages of silicone resin and of fluid silicone being equal to 100.

Preferably, the silicone resin according to the invention is the product of condensation of $SiO_2$ groups and of $R_3(SiO)_{1/2}$ (triorganosilyl) groups for which each group R is independently selected from methyl, ethyl, propyl and vinyl radicals and for which the ratio between the $SiO_2$ functions and the $R_3(SiO)_{1/2}$ functions of the silicone resin ranges from 0.6 to 0.9. Triorganosilyl groups that may be used to form the silicone resin may be trimethylsilyl, triethylsilyl, methylmethylpropylsilyl and dimethylvinylsilyl units, and mixtures thereof. The trimethylsilyl group is preferred in the context of the invention.

Preferably, the fluid silicone according to the invention is a diorganopolysiloxane containing OH end functions, having a viscosity of between 100 and 100 000 cSt at 25° C., for which the substituents of the diorganopolysiloxane are chosen independently from methyl, ethyl, propyl and vinyl radicals. The diorganosiloxanes are preferably linear polymers. Examples of diorganopolysiloxane may be, without limitation, a polydimethylsiloxane, an ethylmethylpolysiloxane, a copolymer of dimethylsiloxane and methylvinylsiloxane, and mixtures of such polymers or copolymers having OH ends. The preferred diorganopolysiloxane is a polydimethylsiloxane.

Examples of synthesis of such a copolymer are described, for example, in patent U.S. Pat. No. 5,162,410 or in patent CA 711 756.

The preferred copolymers according to the invention are sold by Dow Corning under the reference BIO-PSA®, these BIO-PSA® copolymers themselves possibly being in two forms, standard or amine-compatible, and being supplied in different solvents with several silicone resin/fluid silicone ratios. Mention may be made especially of the grades 7-4400, 7-4500 and 7-4600. The Bio-PSA® that is particularly preferred according to the invention is the grade 7-4400.

vii) Reactive silicones

The hydrophobic film-forming polymer may be chosen from polymers obtained from silicone compounds X and Y that are capable of reacting together at the time of application to form the hydrophobic film-forming polymer. The term "silicone compound" means a compound comprising at least two organosiloxane units. According to one particular embodiment, compounds X and compounds Y are silicone compounds. The compounds X and Y may be amino or non-amino compounds. They may comprise polar groups that may be chosen from the following groups: —COOH, —COO⁻, —COO—, —OH, —NH$_2$, —NH—, —NR—, —SO$_3$H, —SO$_3$⁻, —OCH$_2$CH$_2$—, —O—CH$_2$CH$_2$CH$_2$—, —O—CH$_2$CH(CH$_3$)—, —NR$_3$⁺, —SH, —NO$_2$, I, Cl, Br, —CN, —PO$_4^{3-}$, —CONH—, —CONR—, —CONH$_2$, —CSNH—, —SO$_2$—, —SO—, —SO$_2$NH—, —NHCO—, —NHSO$_2$—, —NHCOO—, —OCONH—, —NHCSO— and —OCSNH—, R representing an alkyl group.

According to another embodiment, at least one of the compounds X and Y is a polymer whose main chain is mainly formed from organosiloxane units.

Among the silicone compounds mentioned hereinbelow, some of them may have both film-forming properties and adhesive properties, depending, for example, on the silicone proportion thereof or on whether they are used as a mixture with a particular additive. It is consequently possible to modify the film-forming properties or the adhesive properties of such compounds according to the intended use, and this is in particular the case for "room-temperature-vulcanizable" reactive elastomeric silicones. Compounds X and Y may react together at a temperature ranging between room temperature and 180° C. Advantageously, compounds X and Y can react together at room temperature (20±5° C.) and atmospheric pressure, advantageously in the presence of a catalyst, via a hydrosilylation reaction, a condensation reaction or a crosslinking reaction in the presence of a peroxide.

Compounds X and Y are capable of reacting via condensation, either in the presence of water (hydrolysis) by reaction of 2 compounds bearing alkoxysilane groups, or via "direct" condensation by reaction of a compound bearing alkoxysilane group(s) and a compound bearing silanol group(s) or by reaction of 2 compounds bearing silanol group(s).

When the condensation is performed in the presence of water, this water may in particular be water provided by an external source, for example premoistening of the hair (for example with a mister).

In this mode of reaction via condensation, compounds X and Y, which may be identical or different, may thus be chosen from silicone compounds whose main chain comprises at least two alkoxysilane groups and/or at least two silanol (Si—OH) groups, on the side and/or at the end of the chain.

In one advantageous embodiment, compounds X and/or Y are chosen from polyorganosiloxanes comprising at least two alkoxysilane groups. The term "alkoxysilane group" means a group comprising at least one —Si—OR portion, R being an alkyl group containing from 1 to 6 carbon atoms.

Compounds X and Y are especially chosen from polyorganosiloxanes comprising alkoxysilane end groups, more specifically those comprising at least 2 alkoxysilane end groups and preferably trialkoxysilane end groups.

Such polymers are described especially in documents U.S. Pat. Nos. 3,175,993, 4,772,675, 4,871,827, 4,888,380, 4,898,910, 4,906,719 and 4,962,174, and WO 01/96450.

When the film-forming polymer according to the invention is dispersed in the organic solvent, the composition according to the invention advantageously comprises at least one stable dispersion of essentially spherical polymer particles of one or more polymers. Before incorporating them into the composition of the invention, the particles are generally dispersed in a physiologically acceptable liquid fatty phase, such as hydrocarbon-based oils or silicone oils. According to one embodiment, these dispersions are generally known as NADs (non-aqueous dispersions) of polymer, as opposed to networks, which are aqueous dispersions of polymer.

These dispersions may especially be in the form of polymer nanoparticles in stable dispersion in the said liquid organic phase. The nanoparticles preferably have a mean size of between 5 and 800 nm and better still between 50 and 500 nm. It is possible, however, to obtain polymer particle sizes ranging up to 1 μm.

The polymers in dispersion that may be used in the composition of the invention preferably have a molecular weight ranging from about 2000 to 10 000 000 and a Tg ranging from −100° C. to 300° C. and preferably from −10° C. to 80° C.

Among the film-forming polymers in dispersion that may be mentioned are radical, acrylic or vinyl homopolymers or copolymers, preferably with a Tg of less than or equal to 40° C. and especially ranging from −10° C. to 30° C., used alone or as a mixture.

According to one embodiment, the polymer particles are stabilized with a stabilizer that is solid at room temperature, which may be a block polymer, a grafted polymer and/or a statistical polymer, alone or as a mixture. The stabilization may take place by any known means, and in particular by direct addition of the stabilizing polymer during the polymerization.

When an aqueous dispersion of polymer particles is used, the solids content of the said aqueous dispersion may be from about 3% to 60% and preferably from 10% to 50% by weight.

The size of the polymer particles in aqueous dispersion may be between 10 and 500 nm and is preferably between 20 and 150 nm, allowing the production of a film of noteworthy gloss. However, particle sizes ranging up to 1 micron may be used.

In a non-limiting manner, the preferred film-forming polymers are chosen from the following polymers or copolymers: polyurethanes, polyurethane-acrylics, polyureas, polyurea-polyurethanes, polyester-polyurethanes, polyether-polyurethanes, polyesters, polyester amides; acrylic and/or vinyl polymers or copolymers; acrylic-silicone copolymers; polyacrylamides; silicone polymers such as silicone polyurethane or acrylic polymers, fluoro polymers; celluloses; and mixtures thereof.

The hydrophobic film-forming polymers according to the invention may be selected on the basis of their mechanical properties. Such properties may be the flexibility, the hardness, the adhesion, the remanence, the resistance to water or to other chemical compounds, and the abrasion resistance. It is also possible to take advantage of the more versatile properties of block polymers (polymers constituted of two or more distinct polymer segments), grafted polymers (polymers containing a polymeric side chain grafted onto the homopolymer or copolymer backbone) or heteropolymers (polymers comprising two or more different monomers). In the copolymers, for example, the amount of hard and soft blocks has a significant impact on the properties of the polymer.

Furthermore, it is possible to mix two or more polymers in order to achieve the desired property. Examples of combinations may be polyurethane and polyacrylates, polyurethane and polyesters, two polymers having a silicone portion, or polyurethane and a polymer having a silicone portion.

According to one particular embodiment, the hydrophobic film-forming polymer is a nonionic polymer. According to another embodiment, the film-forming polymer is solid at 25° C., in the sense that no flowing is observed with the naked eye after one hour.

According to an advantageous embodiment, the hydrophobic film-forming polymer is chosen from hybrid acrylic polymers, preferably in the form of particles in aqueous dispersion, preferably chosen from copolymers of (meth) acrylic acid ester(s) and of styrene, as described above, linear block silicone copolymers, silicone copolymers obtained by reaction of a silicone resin and of a fluid silicone, as described above, and mixtures thereof.

The hydrophobic film-forming polymer(s) may be present in a solids content (or active material content) ranging from 0.1% to 40% by weight, preferably ranging from 0.1% to 30% by weight, preferably ranging from 0.5% to 20% by weight and preferentially ranging from 1% to 20% by weight relative to the total weight of each first and second composition.

According to one embodiment, the first and second compositions of the process according to the invention each comprise as hydrophobic film-forming polymers at least one hybrid acrylic polymer, preferably in the form of particles in aqueous dispersion, as described above, preferably chosen from copolymers of (meth)acrylic acid ester(s) and of styrene, and at least one linear block silicone copolymer as described above.

Also preferably in this embodiment, the hybrid hydrophobic film-forming acrylic polymer or polymers and the linear block silicone copolymer or copolymers are present in each composition in a hybrid hydrophobic film-forming acrylic polymer(s) to linear block silicone copolymer(s) ratio by weight (as polymeric active materials) ranging from 0.2 to 10, better still from 0.5 to 5 and even better still from 1 to 3.

When the hybrid hydrophobic film-forming acrylic polymer has a glass transition temperature which is too high for the desired use, for example a Tg above 40° C., a plasticizer can be combined therewith so as to lower this temperature of the mixture used. The plasticizer can be chosen from the plasticizers normally used in the field of application and in particular from compounds which can be solvents for the polymer. Preferably, the plasticizer has a molecular weight of less than or equal to 5000 g/mol, preferably of less than or equal to 2000 g/mol, preferably of less than or equal to 1000 g/mol and more preferably of less than or equal to 900 g/mol. The plasticizer advantageously has a molecular weight of greater than or equal to 100 g/mol.

Thus, the composition may also comprise at least one plasticizer. In particular, mention may be made, alone or as a mixture, of the usual plasticizers, such as:
  glycols and derivatives thereof, such as diethylene glycol ethyl ether, diethylene glycol methyl ether, diethylene glycol butyl ether or diethylene glycol hexyl ether, ethylene glycol ethyl ether, ethylene glycol butyl ether or ethylene glycol hexyl ether;
  polyethylene glycols, polypropylene glycols, polyethylene glycol-polypropylene glycol copolymers, and mixtures thereof, especially high molecular weight polypropylene glycols, for example having a molecular mass ranging from 500 to 15 000, for instance
  glycol esters,
  propylene glycol derivatives and in particular propylene glycol phenyl ether, propylene glycol diacetate, dipropylene glycol ethyl ether, tripropylene glycol methyl ether, diethylene glycol methyl ether or dipropylene glycol butyl ether. Such compounds are sold by Dow Chemical under the names Dowanol PPH and Dowanol DPnB,
  acid esters, in particular carboxylic acid esters, such as citrates, phthalates, adipates, carbonates, tartrates, phosphates or sebacates,
  esters resulting from the reaction of a monocarboxylic acid of formula $R_{11}COOH$ with a diol of formula $HOR_{12}OH$ with $R_{11}$ and $R_{12}$, which are identical or different, representing a saturated or unsaturated and linear, branched or cyclic hydrocarbon chain preferably comprising from 3 to 15 carbon atoms and optionally comprising one or more heteroatoms, such as N, O or S, in particular the monoester resulting from the reaction of isobutyric acid and octanediol, such as 2,2,4-trimethyl-1,3-pentanediol, such as that sold under the reference Texanol Ester Alcohol by Eastman Chemical,
  oxyethylenated derivatives, such as oxyethylenated oils, especially plant oils, such as castor oil,
  mixtures thereof.

More particularly, the plasticizer may be chosen from esters of at least one carboxylic acid containing 1 to 7 carbon atoms and of a polyol comprising at least 4 hydroxyl groups.

The polyol can be a cyclized or non-cyclized monosaccharide-polyhydroxyaldehyde (aldose) or polyhydroxyketone (ketose). The polyol is preferably a cyclized monosaccharide in the hemiacetal form.

The polyol can be a mono- or polysaccharide comprising from 1 to 10 monosaccharide units, preferably from 1 to 4 monosaccharide units and more preferably one or two monosaccharide units. The polyol can be chosen from erythritol, xylitol, sorbitol, glucose, sucrose, lactose or maltose.

The polyol is preferably a disaccharide. Among the disaccharides, mention may be made of sucrose (also known as α-D-glucopyranosyl-(1-2)-β-D-fructofuranose), lactose (also known as β-D-galactopyranosyl-(1-4)-β-D-glucopyranose) and maltose (also known as α-D-glucopyranosyl-(1-4)-β-D-glucopyranose), and preferably sucrose.

The ester can be composed of a polyol esterified by at least two different monocarboxylic acids or by at least three different monocarboxylic acids.

The ester can be a copolymer of two esters, in particular a copolymer i) of a sucrose substituted by benzoyl groups and ii) of a sucrose substituted by acetyl and/or isobutyryl groups.

The carboxylic acid is preferably a monocarboxylic acid containing from 1 to 7 carbon atoms and preferably from 1 to 5 carbon atoms, chosen, for example, from acetic acid, n-propanoic acid, isopropanoic acid, n-butanoic acid, isobutanoic acid, tert-butanoic acid, n-pentanoic acid and benzoic acid.

The ester may be obtained from at least two different monocarboxylic acids. According to one embodiment, the acid is an unsubstituted linear or branched acid.

The acid is preferably chosen from acetic acid, isobutyric acid and benzoic acid, and mixtures thereof, and more preferentially.

According to one preferred embodiment, the ester is sucrose diacetate hexakis(2-methylpropanoate), such as the product sold under the name Sustane SAIB Food Grade Kosher by the company Eastman Chemical.

According to another embodiment, the plasticizer may be chosen from esters of an aliphatic or aromatic polycarboxylic acid and of an aliphatic or aromatic alcohol containing from 1 to 10 carbon atoms.

The aliphatic or aromatic alcohol comprises from 1 to 10 and preferably from 1 to 8 carbon atoms, for example from 1 to 6 carbon atoms. It may be chosen from the alcohols R1OH, such that R1 represents methyl, ethyl, propyl, isopropyl, butyl, hexyl, ethylhexyl, decyl, isodecyl, benzyl, or benzyl substituted with an alkyl comprising 1 to 3 carbon atoms, and mixtures thereof.

The aliphatic or aromatic polycarboxylic acid preferably contains from 3 to 12 carbon atoms, preferably from 3 to 10 carbon atoms and preferably from 3 to 8 carbon atoms, for example 6 or 8 carbon atoms.

The aliphatic or aromatic polycarboxylic acid is advantageously chosen from dicarboxylic acids and tricarboxylic acids.

Among the aliphatic dicarboxylic acids that may be mentioned are those of formula HOOC—$(CH_2)_n$—COOH, in which n is an integer ranging from 1 to 10 and preferably ranging from 2 to 8, for example equal to 2, 4, 6 or 8.

Preference is given to dicarboxylic acids chosen from succinic acid, adipic acid and sebacic acid.

Mention may be made, among aromatic dicarboxylic acids, of phthalic acid.

Among the tricarboxylic acids, mention may be made of the triacids that correspond to the formula

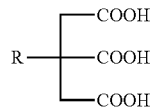

in which R represents an —H, —OH or —OCOR' group in which R' represents an alkyl group having from 1 to 6 carbon atoms. Preferably, R represents a group —$OCOCH_3$. The tricarboxylic acid is especially chosen from acetylcitric acid, butyroylcitric acid and citric acid.

Use may be made, among tricarboxylic acid esters, of esters derived from citric acid (or citrates), such as tributyl acetylcitrate, triethyl acetylcitrate, triethylhexyl acetylcitrate, trihexyl acetylcitrate, trihexyl butyroylcitrate, triisodecyl citrate, triisopropyl citrate, tributyl citrate and tri(2-ethylhexyl) citrate. Mention may be made, as commercial references for plasticizers mentioned above, of the Citroflex range sold by Vertellus, with in particular Citroflex A4 and Citroflex C2.

Mention may be made, among adipic acid esters, of dibutyl adipate and di(2-ethylhexyl) adipate.

Mention may be made, among sebacic acid esters, of dibutyl sebacate, di(2-ethylhexyl) sebacate, diethyl sebacate and diisopropyl sebacate.

Mention may be made, among succinic acid esters, of di(2-ethylhexyl) succinate and diethyl succinate.

Mention may be made, among phthalic acid esters, of benzyl butyl phthalate, dibutyl phthalate, diethylhexyl phthalate, diethyl phthalate and dimethyl phthalate.

Advantageously, the plasticizer may be present in the composition in an amount such that the mass ratio between the hydrophobic film-forming polymer and the plasticizer is between 0.5 and 100, preferably between 1 and 50 and preferably between 1 and 10.

Volatile Solvent

According to the invention, the first and second compositions applied to the hair each contain at least one volatile solvent, which may be identical or different between each composition.

In the context of the invention, the term "volatile solvent" means a compound that is liquid at room temperature (20° C.) and at atmospheric pressure, having a vapour pressure at 20° C. of greater than 0.1 mmHg, preferably between 0.1 and 300 mmHg and even more preferentially between 0.5 and 200 mmHg.

This volatile solvent may be water, a non-silicone organic solvent or a silicone organic solvent, or mixtures thereof. Volatile non-silicone organic solvents that may be mentioned include:

volatile $C_1$-$C_4$ alkanols such as ethanol or isopropanol;

volatile $C_5$-$C_7$ alkanes such as n-pentane, hexane, cyclopentane, 2,3-dimethylbutane, 2,2-dimethylbutane, 2-methylpentane or 3-methylpentane;

esters of liquid $C_1$-$C_{20}$ acids and of volatile $C_1$-$C_8$ alcohols such as methyl acetate, n-butyl acetate, ethyl acetate, propyl acetate, isopentyl acetate or ethyl 3-ethoxypropionate;

ketones that are liquid at room temperature and volatile, such as methyl ethyl ketone, methyl isobutyl ketone, diisobutyl ketone, isophorone, cyclohexanone or acetone;

volatile polyols such as propylene glycol;

volatile ethers such as dimethoxymethane, diethoxyethane or diethyl ether;

volatile glycol ethers such as 2-butoxyethanol, butyl diglycol, diethylene glycol monomethyl ether, propylene glycol n-butyl ether or propylene glycol monomethyl ether acetate;

volatile hydrocarbon-based oils such as volatile hydrocarbon-based oils containing from 8 to 16 carbon atoms, and mixtures thereof, and especially branched $C_8$-$C_{16}$ alkanes, for instance $C_8$-$C_{16}$ isoalkanes (also known as isoparaffins), isododecane, isodecane and, for example, the oils sold under the trade names Isopar or Permethyl, and mixtures thereof. Mention may also be made of isohexyl or isodecyl neopentanoate;

volatile $C_4$-$C_{10}$ perfluoroalkanes such as dodecafluoropentane, tetradecafluorohexane or decafluoropentane;

volatile perfluorocycloalkyls such as perfluoromethylcyclopentane, 1,3-perfluorodimethylcyclohexane and perfluorodecalin, sold, respectively, under the names Flutec PC1®, Flutec PC3® and Flutec PC6® by the company F2 Chemicals, and also perfluorodimethylcyclobutane and perfluoromorpholine;

the volatile fluoroalkyl or heterofluoroalkyl compounds corresponding to the following formula:

$$CH_3-(CH_2)_n-[Z]_t-X-CF_3$$

in which t is 0 or 1; n is 0, 1, 2 or 3; X is a linear or branched divalent perfluoroalkyl radical containing from 2 to 5 carbon atoms, and Z represents O, S or NR, R being hydrogen or a radical $-(CH_2)_n-CH_3$ or $-(CF_2)_m-CF_3$, m being 2, 3, 4 or 5.

Among the volatile fluoroalkyl or heterofluoroalkyl compounds that may especially be mentioned are methoxynonafluorobutane sold under the names MSX 4518® and HFE-7100® by the company 3M, and ethoxynonafluorobutane sold under the name HFE-7200® by the company 3M.

Preferably, the solvent is chosen such that its boiling point is less than 200° C.

According to a particular embodiment, the non-silicone organic solvent is chosen from ethanol, isopropanol, acetone and isododecane.

Volatile silicone solvents that may be mentioned include low-viscosity silicone compounds chosen from linear or cyclic silicones containing from 2 to 7 silicon atoms, these silicones optionally comprising alkyl or alkoxy groups containing from 1 to 10 carbon atoms, for example octamethylcyclotetrasiloxane, decamethylcyclopentasiloxane, dodecamethylcyclohexasiloxane, heptamethylhexyltrisiloxane, heptamethylethyltrisiloxane, heptamethyloctyltrisiloxane, octamethyltrisiloxane and decamethyltetrasiloxane, and mixtures thereof. According to a particular embodiment, the silicone compound is chosen from cyclopentadimethylsiloxane and dodecamethylcyclohexasiloxane.

According to one particular embodiment, the volatile silicone solvent has a viscosity of less than 50 centistokes.

Preferably, the volatile silicone is cyclic and chosen from decamethylcyclopentasiloxane, octamethyltrisiloxane and decamethyltetrasiloxane. Examples include the decamethylcyclopentasiloxane sold under the name DC-245 by the company Dow Corning, the octamethyltrisiloxane sold under the name DC-200 Fluid 1 cSt by the company Dow Corning, and the decamethyltetrasiloxane sold under the name DC-200 Fluid 1.5 cSt by the company Dow Corning.

This cyclic volatile silicone generally has a low viscosity, for example a viscosity of less than 5 cSt at 25° C.

Preferably, the volatile silicone is cyclic and is the decamethylcyclopentasiloxane sold under the name DC-245 by the company Dow Corning.

Preferably, the volatile solvent is chosen from water, non-silicone organic solvents, preferably isododecane, and mixtures thereof.

The volatile solvent(s) may be present in a content ranging from 0.1% to 95% by weight, preferably ranging from 1% to 70% by weight and preferentially ranging from 5% to 90% by weight, relative to the total weight of each first and/or second composition.

Pigments

Each of the first and second compositions comprises one or more pigments, which differ between the two compositions by the nature of at least one pigment and/or by the concentration of at least one pigment.

The term "pigments" means white or coloured particles of any shape, which are insoluble in the composition in which they are present.

The pigments that may be used are chosen especially from organic and/or mineral pigments known in the art, in particular those described in Kirk-Othmer's *Encyclopedia of Chemical Technology* and in Ullmann's *Encyclopedia of Industrial Chemistry*.

They may be natural, of natural origin, or non-natural.

These pigments may be provided in the pigment powder or paste form. They may be coated or uncoated.

The pigments may be chosen, for example, from mineral pigments, organic pigments, lakes, special-effect pigments, such as nacres or glitter flakes, and mixtures thereof. The pigment may be a mineral pigment. The term "mineral pigment" means any pigment that satisfies the definition in Ullmann's encyclopedia in the chapter on mineral pigments. Among the mineral pigments that are useful in the present invention, mention may be made of ochres such as red ochre (clay (in particular kaolinite) and iron hydroxide (for example haematite)), brown ochre (clay (in particular kaolinite) and limonite), yellow ochre (clay (in particular kaolinite) and goethite); titanium dioxide, optionally surface-treated; zirconium oxide or cerium oxide; zinc oxide, iron oxide (black, yellow or red) or chromium oxide; manganese violet, ultramarine blue, chromium hydrate and ferric blue; metal powders such as aluminium powder or copper powder.

Mention may also be made of alkaline-earth metal carbonates (such as calcium carbonate or magnesium carbonate), silicon dioxide, quartz and any other compound used as inert filler in cosmetic compositions, provided that these compounds contribute colour or whiteness to the composition under the conditions in which they are employed.

The pigment may be an organic pigment. The term "organic pigment" means any pigment that satisfies the definition in Ullmann's encyclopaedia in the chapter on organic pigments.

The organic pigment may especially be chosen from nitroso, nitro, azo, xanthene, pyrene, quinoline, anthraquinone, triphenylmethane, fluorane, phthalocyanin, metal complex, isoindolinone, isoindoline, quinacridone, perinone, perylene, diketopyrrolopyrrole, indigo, thioindigo, dioxazine, triphenylmethane and quinophthalone compounds.

Use may also be made of any mineral or organic compound that is insoluble in the composition and standard in cosmetics, provided that these compounds afford the composition colour or whiteness under the conditions in which they are used, for example guanine, which, according to the refractive index of the composition, is a pigment.

In particular, the white or coloured organic pigments may be selected from carmine lake, carbon black, aniline black, azo yellow, quinacridone, phthalocyanine blue, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenolic derivatives as described in patent FR 2 679 771. Examples that may also be mentioned include pigmentary pastes of organic pigments, such as the products sold by the company Hoechst under the names:

Cosmenyl Yellow IOG: Pigment Yellow 3 (CI 11710);
Cosmenyl Yellow G: Pigment Yellow 1 (CI 11680);
Cosmenyl Orange GR: Pigment Orange 43 (CI 71105);
Cosmenyl Red R: Pigment Red 4 (CI 12085);
Cosmenyl Carmine FB: Pigment Red 5 (CI 12490);
Cosmenyl Violet RL: Pigment Violet 23 (CI 51319);
Cosmenyl Blue A2R: Pigment Blue 15.1 (CI 74160);
Cosmenyl Green GG: Pigment Green 7 (CI 74260);
Cosmenyl Black R: Pigment Black 7 (CI 77266).

The pigments in accordance with the invention may also be in the form of composite pigments, as described in patent EP 1 184 426. These composite pigments may be composed in particular of particles comprising a mineral core, at least one binder, which provides for the attachment of the organic pigments to the core, and at least one organic pigment which at least partially covers the core.

The organic pigment may also be a lake. The term "lake" means dyes adsorbed onto insoluble particles, the assembly thus obtained remaining insoluble during use.

The mineral substrates onto which the dyes are adsorbed are, for example, alumina, silica, calcium sodium borosilicate, calcium aluminium borosilicate and aluminium.

Mention may be made, among the dyes, of carminic acid. Mention may also be made of the dyes known under the following names: D&C Red 21 (CI 45380), D&C Orange 5 (CI 45370), D&C Red 27 (CI 45410), D&C Orange 10 (CI 45425), D&C Red 3 (CI 45430), D&C Red 4 (CI 15510), D&C Red 33 (CI 17200), D&C Yellow 5 (CI 19140), D&C Yellow 6 (CI 15985), D&C Green (CI 61570), D&C Yellow 1 O (CI 77002), D&C Green 3 (CI 42053) or D&C Blue 1 (CI 42090).

An example of a lake that may be mentioned is the product known under the following name: D&C Red 7 (CI 15 850:1).

The pigment may also be a special-effect pigment. The term "special-effect pigments" means pigments that generally create a coloured appearance (characterized by a certain shade, a certain vivacity and a certain level of luminance) that is non-uniform and that changes as a function of the conditions of observation (light, temperature, angles of observation, etc.). They thereby contrast with coloured pigments that afford a conventional uniform opaque, semi-transparent or transparent shade.

Several types of special-effect pigment exist: those with a low refractive index, such as fluorescent, photochromic or thermochromic pigments, and those with a higher refractive index, such as nacres, interference pigments or glitter flakes.

Examples of special-effect pigments that may be mentioned include nacreous pigments such as titanium mica or with bismuth oxychloride, coloured nacreous pigments such as titanium mica with iron oxides, titanium mica especially with ferric blue or with chromium oxide, titanium mica with an organic pigment of the abovementioned type, and also nacreous pigments based on bismuth oxychloride. Nacreous pigments that may be mentioned include the nacres Cellini sold by Engelhard (mica-$TiO_2$-lake), Prestige sold by Eckart (mica-$TiO_2$), Prestige Bronze sold by Eckart (mica-$Fe_2O_3$) and Colorona sold by Merck (mica-$TiO_2$—$Fe_2O_3$).

Mention may also be made of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

Mention may also be made, still as examples of nacres, of particles comprising a borosilicate substrate coated with titanium oxide.

Particles comprising a glass substrate coated with titanium oxide are especially sold under the name Metashine MC1080RY by the company Toyal.

Finally, examples of nacres that may also be mentioned include polyethylene terephthalate flakes, especially those sold by the company Meadowbrook Inventions under the name Silver 1P 0.004X0.004 (silver flakes).

It is also possible to envisage multilayer pigments based on synthetic substrates, such as alumina, silica, calcium sodium borosilicate, calcium aluminium borosilicate and aluminium.

The special-effect particles may also be chosen from reflective particles, i.e. especially from particles whose size, structure, especially the thickness of the layer(s) of which they are made and their physical and chemical nature, and surface state, allow them to reflect incident light. This reflection may, where appropriate, have an intensity sufficient to create at the surface of the composition or of the mixture, when it is applied to the support to be made up, points of overbrightness that are visible to the naked eye, i.e. more luminous points that contrast with their environment by appearing to sparkle.

The reflective particles may be selected so as not to significantly alter the colouration effect generated by the colouring agents with which they are combined, and more particularly so as to optimize this effect in terms of colour yield. They may more particularly have a yellow, pink, red, bronze, orange, brown, gold and/or coppery colour or tint.

These particles may have varied forms and may especially be in platelet or globular form, in particular in spherical form.

The reflective particles, whatever their form, may or may not have a multilayer structure and, in the case of a multilayer structure, may have, for example, at least one layer of uniform thickness, in particular of a reflective material.

When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be made of one or more organic and/or mineral materials.

More particularly, it may be chosen from glasses, ceramics, graphite, metal oxides, aluminas, silicas, silicates, especially aluminosilicates and borosilicates, and synthetic mica, and mixtures thereof, this list not being limiting.

The reflective material may comprise a layer of metal or of a metallic material.

Reflective particles are described especially in documents JP-A-09188830, JP-A-10158450, JP-A-10158541, JP-A-07258460 and JP-A-05017710.

Again as an example of reflective particles comprising a mineral substrate coated with a layer of metal, mention may also be made of particles comprising a silver-coated borosilicate substrate.

Particles comprising a glass substrate coated with silver, in the form of platelets, are sold under the name Microglass Metashine REFSX 2025 PS by Toyal. Particles comprising a glass substrate coated with nickel/chromium/molybdenum alloy are sold under the names Crystal Star GF 550 and GF 2525 by this same company.

Use may also be made of particles comprising a metal substrate, such as silver, aluminium, iron, chromium, nickel, molybdenum, gold, copper, zinc, tin, magnesium, steel, bronze or titanium, the said substrate being coated with at least one layer of at least one metal oxide, such as titanium oxide, aluminium oxide, iron oxide, cerium oxide, chromium oxide, silicon oxides and mixtures thereof.

Examples that may be mentioned include aluminium powder, bronze powder or copper powder coated with $SiO_2$ sold under the name Visionaire by the company Eckart. Mention may also be made of pigments with an interference effect not bound to a substrate, for instance liquid crystals (Helicones HC from Wacker), holographic interference flakes (Geometric Pigments or Spectra f/x from Spectratek). Special-effect pigments also comprise fluorescent pigments, whether these are substances which are fluorescent in daylight or which produce ultraviolet fluorescence, phosphorescent pigments, photochromic pigments, thermochromic pigments and quantum dots, for example sold by Quantum Dots Corporation.

Quantum dots are luminescent semiconductor nanoparticles capable of emitting, under light excitation, radiation exhibiting a wavelength of between 400 nm and 700 nm. These nanoparticles are known from the literature. In particular, they may be synthesized according to the processes described, for example, in U.S. Pat. Nos. 6,225,198 or 5,990,479, in the publications which are cited therein and in the following publications: Dabboussi B. O. et al., "(CdSe)ZnS core-shell quantum dots: synthesis and characterization of a size series of highly luminescent nanocrystallites", Journal of Physical Chemistry B, vol. 101, 1997, pp. 9463-9475, and Peng, Xiaogang et al., "Epitaxial growth of highly luminescent CdSe/CdS core/shell nanocrystals with photostability and electronic accessibility", Journal of the American Chemical Society, vol. 119, No. 30, pp. 7019-7029.

The variety of pigments that may be used in the present invention makes it possible to obtain a wide range of colours, and also particular optical effects such as metallic effects or interference effects.

The size of the pigment used in the cosmetic composition according to the present invention is generally between 10 nm and 200 μm, preferably between 20 nm and 80 μm and more preferably between 30 nm and 50 μm.

The pigments may be dispersed in the product by means of a dispersant.

The dispersant serves to protect the dispersed particles against agglomeration or flocculation. This dispersant may be a surfactant, an oligomer, a polymer or a mixture of several thereof, bearing one or more functionalities with strong affinity for the surface of the particles to be dispersed. In particular, they can become attached physically or chemically to the surface of the pigments. These dispersants also contain at least one functional group that is compatible with or soluble in the continuous medium. Use is made in particular of esters of 12-hydroxystearic acid and of $C_8$ to $C_{20}$ fatty acid and of polyol, such as glycerol or diglycerol, such as the stearate of poly(12-hydroxystearic acid) with a molecular weight of approximately 750 g/mol, such as that sold under the name of Solsperse 21 000 by the company Avecia, polyglyceryl-2 dipolyhydroxystearate (CTFA name), sold under the reference Dehymyls PGPH by the company Henkel, or polyhydroxystearic acid, such as that sold under the reference Arlacel P100 by the company Uniqema, and mixtures thereof.

As other dispersants that may be used in the compositions of the invention, mention may be made of quaternary ammonium derivatives of polycondensed fatty acids, for instance Solsperse 17 000 sold by the company Avecia, and polydimethylsiloxane/oxypropylene mixtures such as those sold by the company Dow Corning under the references DC2-5185 and DC2-5225 C.

The pigments used in the cosmetic composition according to the invention may be surface-treated with an organic agent.

Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those described especially in *Cosmetics and Toiletries*, February 1990, vol. 105, pp. 53-64, before being dispersed in the composition that is useful in the invention. These organic agents may be chosen, for example, from waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminium salts of fatty acids, for example aluminium stearate or laurate; metal alkoxides; polyethylene; (meth)acrylic polymers, for example polymethyl methacrylates; polymers and copolymers containing acrylate units; alkanolamines; silicone compounds, for example silicones, polydimethylsiloxanes; organofluorine compounds, for example perfluoroalkyl ethers; fluorosilicone compounds.

The surface-treated pigments that are useful in the cosmetic composition according to the invention may also have been treated with a mixture of these compounds and/or may have undergone several surface treatments.

The surface-treated pigments that are useful in the context of the present invention may be prepared according to surface-treatment techniques that are well known to those skilled in the art, or may be commercially available in the required form.

Preferably, the surface-treated pigments are coated with an organic layer.

The organic agent with which the pigments are treated may be deposited on the pigments by evaporation of solvent, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is especially described in patent U.S. Pat. No. 4,578,266.

Preferably, use will be made of an organic agent covalently bonded to the pigments. The agent for the surface treatment may represent from 0.1% to 50% by weight, preferably from 0.5% to 30% by weight and even more preferentially from 1% to 10% by weight relative to the total weight of the surface-treated pigments.

Preferably, the surface treatments of the pigments are chosen from the following treatments:
a PEG-silicone treatment, such as the AQ surface treatment sold by LCW;
a methicone treatment, for instance the SI surface treatment sold by LCW;
a dimethicone treatment, for instance the Covasil 3.05 surface treatment sold by LCW;
a dimethicone/trimethyl siloxysilicate treatment, for instance the Covasil 4.05 surface treatment sold by LCW;
an aluminium dimyristate treatment, for instance the MI surface treatment sold by Miyoshi;
a perfluoropolymethylisopropyl ether treatment, for instance the FHC surface treatment sold by LCW;
an isostearyl sebacate treatment, for instance the HS surface treatment sold by Miyoshi;
a perfluoroalkyl phosphate treatment, such as the PF surface treatment sold by Daito;
an acrylate/dimethicone copolymer and perfluoroalkyl phosphate treatment, such as the FSA surface treatment sold by Daito;
a polymethylhydrosiloxane/perfluoroalkyl phosphate treatment, such as the FS01 surface treatment sold by Daito;
an acrylate/dimethicone copolymer treatment, such as the ASC surface treatment sold by Daito;
an isopropyl titanium triisostearate treatment, such as the ITT surface treatment sold by Daito;
an acrylate copolymer treatment, for instance the APD surface treatment sold by Daito;
a perfluoroalkyl phosphate/isopropyl titanium triisostearate treatment, for instance the PF+ITT surface treatment sold by Daito.

Preferably, the pigment is chosen from mineral or mixed mineral-organic pigments.

The amount of pigment(s) may range from 0.001% to 30%, more particularly from 0.01% to 20% and preferably from 0.1% to 15% by weight relative to the total weight of each first and second composition.

The first and second compositions of the process of the invention may moreover, independently of each other, contain other non-volatile organic solvents such as:
non-volatile aromatic alcohols such as benzyl alcohol or phenoxyethanol;
non-volatile esters of liquid $C_1$-$C_{20}$ acids and of $C_1$-$C_8$ alcohols, such as isopropyl myristate;
ethylene carbonate, propylene carbonate or butylene carbonate;
non-volatile polyols such as glycerol, ethylene glycol, dipropylene glycol or butylene glycol;
non-volatile glycol ethers, for instance diethylene glycol monoethyl ether or dipropylene glycol mono-n-butyl ether;
non-volatile hydrocarbon-based oils such as isohexadecane;
non-volatile liquid $C_{10}$-$C_{30}$ fatty alcohols such as oleyl alcohol; esters of liquid $C_{10}$-$C_{30}$ fatty alcohols such as benzoates of $C_{10}$-$C_{30}$ fatty alcohols and mixtures thereof; polybutene oil, isononyl isononanoate, isostearyl malate, pentaerythrityl tetraisostearate or tridecyl trimellitate;
non-volatile perfluoro solvents such as perfluoroperhydrophenanthrene, sold under the name Flutec PC11® by the company F2 Chemicals.

Thickener

The first and second compositions that are useful in the process of the invention may each independently comprise at least one thickener. This thickener may be chosen from mineral or organic, polymeric or non-polymeric thickeners, and mixtures thereof. The term "thickener" means a compound that modifies the rheology of the medium into which it is incorporated.

According to a particular embodiment of the invention, the composition comprises at least one mineral thickener.

Preferably, the thickener(s) are chosen from fumed silica and clays, or mixtures thereof.

The fumed silicas may be obtained by high-temperature pyrolysis of a volatile silicon compound in an oxhydric flame, producing a finely divided silica. This process makes it possible in particular to obtain hydrophilic silicas which contain a large number of silanol groups at their surface. Such hydrophilic silicas are sold, for example, under the names Aerosil 130®, Aerosil 200®, Aerosil 255®, Aerosil 300® and Aerosil 380® by Degussa and Cab-O-Sil HS-5®, Cab-O-Sil EH-5®, Cab-O-Sil LM-130®, Cab-O-Sil MS-55® and Cab-O-Sil M-5® by Cabot.

It is possible to chemically modify the surface of said silica via a chemical reaction which brings about a reduction in the number of silanol groups. It is possible in particular to substitute silanol groups with hydrophobic groups; a hydrophobic silica is then obtained.

The hydrophobic groups can be:

trimethylsiloxyl groups, which are obtained in particular by treating fumed silica in the presence of hexamethyldisilazane. Silicas thus treated are known as "Silica silylate" according to the CTFA (6th edition, 1995). They are sold, for example, under the references Aerosil R812® by the company Degussa and Cab-O-Sil TS-530® by the company Cabot.

dimethylsilyloxyl or polydimethylsiloxane groups, which are obtained in particular by treating fumed silica in the presence of polydimethylsiloxane or dimethyldichlorosilane. Silicas thus treated are known as "Silica dimethyl silylate" according to the CTFA (6th edition, 1995). They are sold, for example, under the references Aerosil R972® and Aerosil R974® by the company Degussa and Cab-O-Sil TS-610® and Cab-O-Sil TS-720® by the company Cabot.

The fumed silica preferably has a particle size that may be nanometric to micrometric, for example ranging from about 5 to 200 nm.

Clays are well known products which are described, for example, in the publication "Minéralogie des argiles" [Mineralogy of Clays], S. Caillère, S. Hénin and M. Rautureau, 2nd Edition, 1982, Masson.

Clays are silicates containing a cation that may be chosen from calcium, magnesium, aluminium, sodium, potassium and lithium cations, and mixtures thereof.

Mention may be made, as examples of such products, of clays of the family of the smectites, such as montmorillonites, hectorites, bentonites, beidellites or saponites, and also of the family of the vermiculites, stevensite or chlorites.

These clays can be of natural or synthetic origin. Clays that are cosmetically compatible with and acceptable to keratin materials are preferably used.

Mention may be made, as clay which can be used according to the invention, of synthetic hectorites (also known as laponites), such as the products sold by Laporte under the name Laponite XLG, Laponite RD and Laponite RDS (these products are sodium magnesium silicates and in particular lithium magnesium sodium silicates); bentonites, such as the product sold under the name Bentone HC by Rheox; magnesium aluminium silicates, in particular hydrated, such as the product sold by R.T. Vanderbilt Company under the name Veegum Ultra, or calcium silicates and in particular that in synthetic form sold by the company Celite & Walsh under the name Micro-Cel C.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkylaryl sulfonates and amine oxides, and mixtures thereof.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; and quaternium-18/benzalkonium bentonite, such as those sold under the names Claytone HT and Claytone PS by Southern Clay.

The thickener may also be chosen from organic compounds.

Mention may be made, for example, of the following polymeric or non-polymeric products:

$C_{10}$-$C_{30}$ fatty amides such as lauric acid diethanolamide, the polyglyceryl (meth)acrylate polymers sold under the names Hispagel and Lubragel by the companies Hispano Quimica or Guardian, polyvinylpyrrolidone, polyvinyl alcohol, crosslinked acrylamide polymers and copolymers, such as those sold under the names PAS 5161 or Bozepol C by the company Hoechst, Sepigel 305 by the company SEPPIC, or the crosslinked methacryloyloxyethyltrimethylammonium chloride homopolymers sold under the name Salcare SC95 by Allied Colloid, associative polymers and in particular associative polyurethanes.

Such thickeners are especially described in patent application EP-A-1 400 234.

Mention may also be made of the following thickeners, in particular if the compositions comprise oily compounds:

organophilic clays;

hydrophobic fumed silicas.

More specifically, organophilic clays are clays modified with chemical compounds which make the clay capable of swelling.

Preferably, each of the first and second compositions comprises at least one thickener, preferably a mineral thickener, which is preferably chosen from clays and even more advantageously from smectites, preferably bentonites.

This or these thickener(s) may then be present in a total content ranging from 0.1% to 10% by weight relative to the weight of each first and/or second composition.

The compositions may also contain at least one agent usually used in cosmetics other than the compounds already mentioned, chosen, for example, from reducing agents, fatty substances, plant oils, softeners, antifoams, moisturizers, UV-screening agents, peptizers, solubilizers, anionic, cationic, nonionic or amphoteric surfactants, proteins, vitamins, propellants, oxyethylenated or non-oxyethylenated waxes, $C_{10}$-$C_{30}$ fatty acids such as stearic acid or lauric acid, and fragrances.

The above additives are generally present in an amount for each of them of between 0.01% and 20% by weight, relative to the weight of the composition.

Needless to say, a person skilled in the art will take care to select this or these optional additive(s) such that the advantageous properties intrinsically associated with the formation of the coating in accordance with the invention are not, or are not substantially, adversely affected.

The first and second compositions according to the invention may each independently be especially in the form of a suspension, a dispersion, a gel, an emulsion, especially an oil-in-water (O/W), water-in-oil (W/O) or multiple (W/O/W or polyol/O/W or O/W/O) emulsion, a cream, a foam, a stick, a dispersion of vesicles, in particular of ionic or nonionic lipids, a two-phase or multiphase lotion, a spray or a paste.

A person skilled in the art may select the appropriate galenical form, and also the method for preparing it, on the basis of his general knowledge, taking into account firstly the nature of the constituents used, especially their solubility in the support, and secondly the intended use of the composition.

The first and second compositions described above may be used on dry or wet keratin fibres and also on any type of fibre, light or dark, natural or dyed, and permanent-waved, bleached or relaxed.

Application Device

According to one embodiment, the first and second compositions used in the process according to the invention are each conditioned in a container comprising a removable applicator comprising a permeable material through which the composition can pass; the composition being applied by placing the applicator in contact with the wet or dry fibres.

By using such a device, the treatment composition it contains can be applied simply, without risk of running of the product, whether in the case of a self-application or of a treatment performed by another person. The application is fast and efficient, without requiring the use of additional accessories, and the impregnation of the fibres is homogeneous.

Such a device is especially described in patent U.S. Pat. No. 5,961,665 (Fishmann).

As indicated hereinabove, the composition is present in a container closed by a removable applicator end piece comprising a permeable material through which the said composition can pass and then by a removable stopper fitted to the said applicator on the container.

Advantageously, the container comprising the composition can comprise an annular narrowing to help it to be grasped in the hand.

The application device can, for example, comprise a container in the form of a small flexible or rigid bottle. Alternatively, a bottle made of thermoplastic material, for example of PET, can be used. The bottle has, for example, a capacity of 6 ml. The bottle comprises a side wall in the form of a comprises a cylindrically axisymmetric side wall, one end of which is closed by a base. The second end is formed by a portion having a narrowed diameter, which ends in a free edge defining an opening.

An applicator end piece is provided to be fitted onto the bottle and to be snap-fastened or screwed onto the above-mentioned opening of the bottle.

The end piece is provided in the form of a substantially cylindrical shell having a uniform circular diameter over a large part of its length. It could have any other form, for example a frustoconical form, becoming progressively smaller until it defines a circular portion.

The end piece has, for example, a diameter of approximately 15 mm. Axial ribs can be provided on the internal wall of the shell. They can comprise a radial indentation which, in the fitted position of the shell, will become housed in the opening of the bottle, thereby allowing the shell to be snap-fastened onto the bottle. Alternatively, it is possible to provide for the inside wall of the shell to be provided with a thread provided to engage with a thread provided on the neck of the bottle.

The applicator end piece can comprise a cylindrical skirt, which provides sealing between the opening of the bottle and the outlet orifice.

The applicator end piece is advantageously obtained by moulding a single piece of a preferably thermoplastic material, in particular of a polyethylene, of a polypropylene, of a polyethylene terephthalate, of a polyvinyl chloride or of a polyamide.

The applicator, in particular in the form of a pad, makes it possible to regulate the flow of composition which it allows to pass, and to prevent it from running.

Advantageously, the applicator, in particular pad, comprises a valve stem and an integral spring which makes possible the dispensing of an appropriate amount of composition.

The permeable material through which the dye composition can pass may be a felt, a flock coating, a foam or an end piece of roll-on type (the roll-on may be a sphere or a cylinder or else may have an ovoid shape of the rugby ball type) and preferably a foam, preferably a polymeric foam, for example made of polyurethane.

For use, the stopper is removed in order to allow the product to be applied by the applicator.

The user takes hold of the bottle, inverts it or tips it and applies the end piece to the fibres to be coloured. It then suffices for the user to apply pressure, one or more times, to the applicator end piece (padding).

According to an alternative which is not represented, the geometric articulation axis is defined by a single film hinge, while the elastic return is ensured by two lateral connecting strips positioned on either side of the film hinge. The choice of such and such a configuration depends to a large extent on the cross section of the container. When the connecting member does not comprise a connecting means, the cover can be welded, moulded or adhesively bonded to a ring or to a fingerstall, into which at least one finger can be inserted. In this case, the ring or the fingerstall is slipped onto the thumb of a hand of the user and the application means is gripped between the other fingers of the same hand. The lock to be coated is positioned next to the membrane of the application means. The thumb is bent in order to pinch the lock between the membrane and the cover. Manual pressure is exerted along the axis of the container and perpendicular to the membrane. The user moves his hand away from the head while maintaining this pressure. He releases the said pressure in order to stop the dyeing of the lock.

With the device according to the invention, the hand (for the hairdresser or a person) can be positioned in the manner most appropriate to the choice of the user.

In the process according to the invention, the first and second compositions described above may be used on dry or wet keratin fibres and also on any type of fibre, light or dark, natural or dyed, and permanent-waved, bleached or relaxed.

The process according to the invention comprises, after application of the first composition to the keratin fibres, and before application of the second composition, a step of drying in the open air or using a device such as a hairdryer, for example at a temperature of greater than or equal to 30° C. According to a particular embodiment, this temperature is greater than 40° C. According to a particular embodiment, this temperature is greater than 45° C. and less than 220° C.

The drying, if it is performed, may be performed immediately after the application of the first composition or after a leave-on time that may range from 1 minute to 30 minutes.

Preferably, if the fibres are dried, then in addition to supplying heat, they are dried with a flow of air. This flow of air during drying makes it possible to improve the individualization of the coating.

During the drying, a mechanical action can be exerted on the locks, such as combing, brushing or running the fingers through the hair. This operation may similarly be performed once the fibres have been dried, naturally or otherwise.

The drying step of the process of the invention may be performed with a hood, a hairdryer, a straightening iron, a Climazon, etc.

When the drying step is performed with a hood or a hairdryer, the drying temperature is between 40 and 110° C. and preferably between 50 and 90° C.

According to one embodiment, after application of the first and second compositions, the fibres may be left to dry or dried, under the same conditions as described above. After drying, the head of hair may be shaped by the fingers or by using a device such as a comb, a brush, straightening tongs or a crimping iron. After such a treatment of the fibres, the shape given is shampoo-fast.

When the drying step is performed with a straightening or crimping iron, the drying temperature is between 110 and 220° C. and preferably between 140 and 200° C.

The examples that follow illustrate the invention in a non-limiting manner. Unless otherwise mentioned, the amounts are expressed as mass percentages.

EXAMPLES

Example 1

Application to Dark Hair

| Composition A | |
|---|---|
| BioPSA DC 7-4405 at 40% in isododecane, sold by Dow Corning | 17.5 g |
| α,ω-Dihydroxylated PDMS gum of high molecular weight (Xiameter PMX-1502 Fluid from Dow Corning) | 1.5 g |
| Mica nacre coated with brown iron oxide, sold by Eckart under the name Prestige Soft Bronze | 6 g |
| Isododecane | qs 100 g |

| Composition B | |
|---|---|
| BioPSA DC 7-4405 at 40% in isododecane, sold by Dow Corning | 17.5 g |
| α,ω-Dihydroxylated PDMS gum of high molecular weight (Xiameter PMX-1502 Fluid from Dow Corning) | 1.5 g |
| Silica-brown iron oxide nacre sold by Merck under the name Prestige Xirona Red | 10 g |
| Isododecane | qs 100 g |

The following tests are then performed on locks of dark hair with a tone depth of 2:
  on a first lock of dark hair, a coat of composition A is applied by finger or with an applicator,
  on a second lock of dark hair, a coat of composition B is applied,
  on a third lock of dark hair, a coat of composition A is applied and is left to dry in the open air until fully dry, followed by a coat of composition B,
each lock is then dried with a hairdryer at a temperature of 80° C. for 2 minutes.

The colorimetric parameters of the various locks are measured and the ΔE is calculated according to the method indicated in the description.

The following results are obtained:

| | L* | a* | b* | ΔE1 | ΔE2 | Colour |
|---|---|---|---|---|---|---|
| Untreated lock | 17.86 | 1.44 | 1.04 | 15.03 | — | 1.78 Brown (tone depth 2) |
| Lock dyed with composition A | 29.52 | 5.86 | 9.44 | | 7.29 | 11.1 Chestnut brown |
| Lock dyed with A and then with B | 29.37 | 13.03 | 10.78 | | | 16.91 Orange |
| Lock dyed with composition B | 23.05 | 14.29 | 6.02 | — | | 15.51 Red |

Treatment of the hair with composition A leads to an optical lightening effect. The application of composition B onto composition A then makes it possible to obtain the desired shade.

A colour that withstands water, styling and touching and that is shampoo-fast is finally obtained on the lock dyed with compositions A and B.

Example 2

Application to Light-Coloured Hair

| Composition C | |
|---|---|
| Styrene/acrylates copolymer in aqueous dispersion, sold by BASF under the name Joncryl 77 | 21.2 g, i.e. 10 g as AM |
| Divinyl dimethicone/dimethicone copolymer in aqueous emulsion, sold by Dow Corning under the reference HMW 2220 Nonionic Emulsion | 8.3 g, i.e. 5 g as AM |
| Clay (Magnesium Aluminium Silicate), sold by Vanderbilt under the name Veegum granules | 2 g |
| Black 2 as an aqueous dispersion, from Daito Kasei Kogyo under the name WD-CB2 | 10 g, i.e. 2.5 g as AM |
| Water | qs 100 g |

| Composition D | |
|---|---|
| Styrene/acrylates copolymer in aqueous dispersion, sold by BASF under the name Joncryl 77 | 21.2 g, i.e. 10 g as AM |
| Divinyl dimethicone/dimethicone copolymer in aqueous emulsion, sold by Dow Corning under the reference HMW 2220 Nonionic Emulsion | 8.3 g, i.e. 5 g as AM |
| Clay (Magnesium Aluminium Silicate), sold by Vanderbilt under the name Veegum granules | 2 g |
| Mica nacre coated with brown iron oxide, sold by Eckart under the name Prestige Soft Bronze | 6 g |
| Water | qs 100 g |

The following tests are then performed on locks of light hair with a tone depth of 8:
  on a first lock of light hair, a coat of composition C, which may be dried with a hairdryer at a temperature of 80° C. or left to dry in the open air, is applied by finger or with an applicator,
  on a second lock of light hair, a coat of composition D, which may be dried with a hairdryer at a temperature of 80° C. or left to dry in the open air, is applied,
  on a third lock of light hair, a coat of composition C is applied, and is left to dry in the open air or may be dried at a temperature of 80° C., followed by a coat of composition D, which is dried in the open air or at a temperature of 80° C.

The colorimetric parameters of the various locks are then measured and the ΔE is calculated according to the method indicated in the description.

The following results are obtained:

| | L* | a* | b* | ΔE1 | ΔE2 | C* | Colour |
|---|---|---|---|---|---|---|---|
| Untreated lock | 43.88 | 3.74 | 15.3 | 30.7 | | 15.75 | Blonde (tone depth 8) |
| Lock dyed with composition C | 16.69 | 0.45 | 1.39 | | 14.16 | 1.47 | Black |
| Lock dyed with C and then with D | 28.13 | 4.43 | 8.73 | | | 9.79 | Chestnut brown |
| Lock dyed with composition D | 43.03 | 13.85 | 20.26 | — | | 24.54 | Orange/hazel |

The application of composition C leads to optical darkening of the lock of hair with a tone depth of 8. The application of composition D onto composition C then makes it possible to obtain the desired shade.

A colour that withstands water, styling and touching and that is shampoo-fast is finally obtained on the lock dyed with compositions C and D.

The invention claimed is:

1. A process for dyeing keratin fibers comprising:
(1) (a) applying to untreated keratin fibers a first composition (i) comprising:
from 1% to 20% of a mixture of at least two hydrophobic film-forming polymers comprising at least one first hydrophobic film-forming polymer chosen from hybrid acrylic hydrophobic polymers and at least one second hydrophobic film-forming polymer chosen from silicone copolymers obtained by reaction of a silicone resin and of a fluid silicone or linear block silicone copolymers,
at least one volatile solvent chosen from water, non-silicone organic solvents, or mixtures thereof, and
from 0.1% to 15% of at least one first pigment chosen from mineral pigments, organic pigments, lakes, special-effect pigments, or mixtures thereof, thereby obtaining keratin fibers having a first coat formed by the first composition (i);
wherein all amounts are by weight, relative to the total weight of the first composition (i); and
(b) drying the first coat; and
(2) applying a second composition (ii) to the keratin fibers having the first coat after the first coat is dried, thereby obtaining keratin fibers having a second coat formed by the second composition (ii) on the first coat, the second composition (ii) comprising:
from 1% to 20% of a mixture of at least two hydrophobic film-forming polymers comprising at least one first hydrophobic film-forming polymer chosen from hybrid acrylic hydrophobic polymers and at least one second hydrophobic film-forming polymer chosen from silicone copolymers obtained by reaction of a silicone resin and of a fluid silicone or linear block silicone copolymers,
at least one volatile solvent chosen from water, non-silicone organic solvents, or mixtures thereof, and
from 0.1% to 15% of at least one second pigment chosen from mineral pigments, organic pigments, lakes, special-effect pigments, or mixtures thereof;
wherein all amounts are by weight, relative to the total weight of the second composition (ii);
wherein the at least one first pigment contained in the first composition (i) and the at least one second pigment contained in the second composition (ii) are qualitatively and/or quantitatively different; and
wherein the first composition (i) produces a coloration such that a color variation ΔE1, expressed in the CIE L* a* b* system, between the keratin fibers having the first coat and the untreated keratin fibers is at least 2, and the second composition (ii) produces a coloration such that a color variation ΔE2, expressed in the CIE L* a* b* system, between the keratin fibers having the second coat and the keratin fibers having the first coat is at least 2.

2. The process according to claim 1, wherein the hybrid acrylic hydrophobic polymers in the first composition (i), the second composition (ii), or both, are independently chosen from hybrid acrylic polymers synthesized from (I) at least one monomer bearing at least one (meth)acrylic acid group, and esters and/or amides of these acid monomers, and (II) at least one styrene compound.

3. The process according to claim 1, wherein the linear block silicone copolymers in the first composition (i), the second composition (ii), or both, are in the form of particles in dispersion in an aqueous medium.

4. The process according to claim 3, wherein the linear block silicone copolymers in the first composition (i), the second composition (ii), or both, are independently obtained by a chain extension reaction, in the presence of a catalyst, of:
(a) at least one polysiloxane (i) having at least one reactive group per molecule; and
(b) at least one organosilicone compound (ii) which reacts with the polysiloxane (i) by a chain extension reaction.

5. The process according to claim 4, wherein the polysiloxane (i) is chosen from compounds of formula (I):

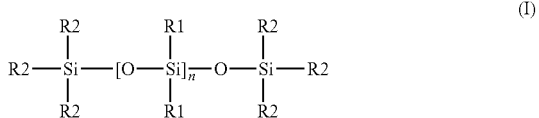

wherein:
R$_1$ and R$_2$ are independently chosen from a hydrocarbon-based group containing from 1 to 20 carbon atoms, an aryl group, or a reactive group,
n is equal to an integer greater than 1,
with the proviso that there are at least one and no more than two reactive groups per polymer, and the reactive groups are independently chosen from hydrogen; aliphatically unsaturated groups; hydroxyl groups; alkoxy groups; alkoxyalkoxy groups; acetoxy groups; amine groups; or mixtures thereof.

6. The process according to claim 5, wherein R$_1$ represents a methyl group and the R$_2$ at one or both end of the chain represents a vinyl group.

7. The process according to claim 5, wherein the at least one organosilicon compound (ii) is chosen from polysiloxanes of formula (I) or compounds acting as chain extenders.

8. The process according to claim 7, wherein the at least one organosilicon compound (ii) is a liquid organohydrogenopolysiloxane of formula (II):

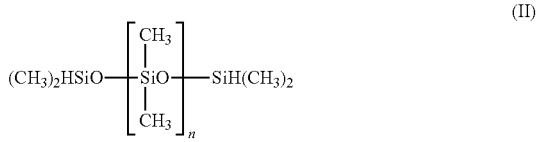

wherein n is an integer greater than 1.

9. The process according to claim 3, wherein the dispersion is an aqueous dispersion of divinyl dimethicone/dimethicone copolymer.

10. The process according to claim 1, wherein the first composition (i), the second composition (ii), or both, independently comprise hydrophobic film-forming polymers chosen from copolymers of (meth)acrylic acid ester(s) and styrene, divinyl dimethicone/dimethicone copolymer, or mixtures thereof.

11. The process according to claim 1, wherein the at least one volatile solvent in the first composition (i), the second composition (ii), or both, is independently chosen from water, ethanol, isopropanol, acetone, isododecane, decamethylcyclopentasiloxane, octamethyltrisiloxane, decamethyltetrasiloxane, or mixtures thereof.

12. The process according to claim 1, wherein the first composition (i), the second composition (ii), or both, comprise at least one thickener.

13. The process according to claim 12, wherein the at least one thickener in the first composition (i), the second composition (ii), or both, is independently chosen from clays.

14. The process according to claim 1, wherein the first composition (i), the second composition (ii), or both, comprise one or more surface-treated pigments.

15. The process according to claim 1, wherein a coloration produced by the first composition (i) when applied to untreated keratin fibers is different from a coloration produced by the second composition (ii) when applied to the keratin fibers having the first coat.

\* \* \* \* \*